(12) United States Patent
Nagalla et al.

(10) Patent No.: US 8,168,396 B2
(45) Date of Patent: May 1, 2012

(54) METHODS FOR DETECTING PRE-DIABETES AND DIABETES USING DIFFERENTIAL PROTEIN GLYCOSYLATION

(75) Inventors: Srinivasa R. Nagalla, Hillsboro, OR (US); Charles T. Roberts, Portland, OR (US)

(73) Assignee: DiabetOmics, LLC, Beaverton, OR (US)

( * ) Notice: Subject to any disclaimer, the term of this patent is extended or adjusted under 35 U.S.C. 154(b) by 0 days.

(21) Appl. No.: 12/777,955

(22) Filed: May 11, 2010

(65) Prior Publication Data

US 2010/0285498 A1    Nov. 11, 2010

Related U.S. Application Data

(60) Provisional application No. 61/177,130, filed on May 11, 2009.

(51) Int. Cl.
    *G01N 33/53* (2006.01)
(52) U.S. Cl. .................................. 435/7.1; 436/518
(58) Field of Classification Search .................. None
    See application file for complete search history.

(56) References Cited

U.S. PATENT DOCUMENTS

| | | | |
|---|---|---|---|
| 4,168,146 A | 9/1979 | Grubb et al. |
| 4,246,339 A | 1/1981 | Cole et al. |
| 4,275,149 A | 6/1981 | Litman et al. |
| 4,277,560 A | 7/1981 | Gray et al. |
| 4,313,734 A | 2/1982 | Leuvering |
| 4,366,241 A | 12/1982 | Tom et al. |
| 4,371,374 A | 2/1983 | Cerami et al. |
| 4,373,932 A | 2/1983 | Gribnau et al. |
| 4,435,504 A | 3/1984 | Zuk et al. |
| 4,496,654 A | 1/1985 | Katz et al. |
| 4,632,901 A | 12/1986 | Valkirs et al. |
| 4,703,017 A | 10/1987 | Campbell et al. |
| 4,740,468 A | 4/1988 | Weng et al. |
| 4,743,560 A | 5/1988 | Campbell et al. |
| 4,770,853 A | 9/1988 | Bernstein |
| 4,775,636 A | 10/1988 | Moeremans et al. |
| 4,806,311 A | 2/1989 | Greenquist |
| 4,806,312 A | 2/1989 | Greenquist |
| 4,812,293 A | 3/1989 | McLaurin et al. |
| 4,855,240 A | 8/1989 | Rosenstein et al. |
| 4,857,453 A | 8/1989 | Ullman et al. |
| 4,861,711 A | 8/1989 | Friesen et al. |
| 4,920,046 A | 4/1990 | McFarland et al. |
| 4,943,522 A | 7/1990 | Eisinger et al. |
| 4,945,042 A | 7/1990 | Geiger et al. |
| 4,954,452 A | 9/1990 | Yost et al. |
| 5,001,049 A | 3/1991 | Klein et al. |
| 5,073,484 A | 12/1991 | Swanson et al. |
| 5,075,078 A | 12/1991 | Osikowicz et al. |
| 5,120,643 A | 6/1992 | Ching et al. |
| 5,126,241 A | 6/1992 | Schenk |
| 5,229,073 A | 7/1993 | Luo et al. |
| 5,279,935 A | 1/1994 | Nycz |
| 5,424,193 A | 6/1995 | Pronovost et al. |
| 5,451,504 A | 9/1995 | Fitzpatrick et al. |
| 5,451,507 A | 9/1995 | Skold et al. |
| 5,591,645 A | 1/1997 | Rosenstein |
| 5,712,172 A | 1/1998 | Huang et al. |
| 5,798,273 A | 8/1998 | Shuler et al. |
| 6,001,658 A | 12/1999 | Fredrickson |
| 6,258,548 B1 | 7/2001 | Buck |
| 6,283,761 B1 | 9/2001 | Joao |
| 6,368,876 B1 | 4/2002 | Huang et al. |
| 6,555,390 B2 | 4/2003 | Chandler |
| 6,656,744 B2 | 12/2003 | Pronovost et al. |
| 6,699,722 B2 | 3/2004 | Bauer et al. |
| 6,716,592 B1 | 4/2004 | Rademacher et al. |
| 7,183,118 B2 | 2/2007 | Aebersold et al. |
| 2003/0049857 A1 | 3/2003 | Chan |
| 2004/0241876 A1 | 12/2004 | Fannes |

FOREIGN PATENT DOCUMENTS

| | | |
|---|---|---|
| EP | 0296724 A2 | 12/1988 |
| EP | 0299428 A2 | 1/1989 |
| EP | 0810436 A1 | 12/1997 |
| WO | 88/08534 A1 | 11/1988 |
| WO | 92/12428 A1 | 7/1992 |
| WO | 94/01775 A1 | 1/1994 |
| WO | 95/16207 A1 | 6/1995 |
| WO | 97/06439 A1 | 2/1997 |
| WO | 98/36278 A1 | 8/1998 |
| WO | 01/40796 A2 | 6/2001 |
| WO | 2007/123951 A2 | 11/2007 |
| WO | 2008/030546 A2 | 3/2008 |
| WO | 2008/055242 A2 | 5/2008 |
| WO | 2009/028880 A2 | 3/2009 |

OTHER PUBLICATIONS

Poland, Dennis C.W. et al., "Increased alpha 3-Fucosylation of alpha 1-acid Glycoprotein in Type I Diabetic Patients is Related to Vascular Function," Glycoconjugate Journal, 2001, vol. 18, pp. 261-268.
Carlsson, Jenny et al., "Detection of Global Glycosylation Changes of Serum Proteins in Type 1 Diabetes Using a Lectin Panel and Multivariate Data Analysis," Talanta, 2008, vol. 76, pp. 333-337.
Buse, Maria G. et al., "Enhanced O-GlcNAc Protein Modification is Associated with Insulin Resistance in GLUT1-Overexpressing Muscles," Am J Physiol Endocrinol Metab, 2002, vol. 283, pp. E241-E250.
Higai, Koji et al., "Altered Glycosylation of alpha1-acid Glycoprotein in Patients with Inflammation and Diabetes Mellitus," Clinica Chimica Acta, 2003, vol. 329, pp. 117-125.
Wang, Linjie et al., "Concanavalin A-captured Glycoproteins in Healthy Human Urine," Molecular & Cellular Ptoteomics 5.3, 2006, pp. 560-562.

(Continued)

*Primary Examiner* — Jacob Cheu
(74) *Attorney, Agent, or Firm* — Schwabe, Williamson & Wyatt

(57) ABSTRACT

Methods for identifying individuals who are not yet diabetic (pre-diabetic), but who are at significant risk of developing diabetes, such as type 2 diabetes, are disclosed herein. Methods are also provided for the identification of diabetic subjects. Also disclosed are methods for identifying individuals with diabetic complications. The methods include the identification of an overall glycosylation profile of proteins in a biological fluid, such as saliva, urine, or serum. In some examples, the methods include determining the amount of one or more protein in a biological fluid or determining the glycosylation pattern of one or more proteins in a biological fluid.

29 Claims, 7 Drawing Sheets

OTHER PUBLICATIONS

Van Dijk, W. et al., "Alpha1-Acid Glycoprotein (Orosomucoid): Pathophysiological Changes in Glycosylation in Relation to its Function," Glycoconjugate Journal, 1995, vol. 12, pp. 227-233.

Pan, Tao et al., "Novel Antibody-Lectin Enzyme-Linked Immunosorbent Assay that Distinguishes Prion Proteins in Sporadic and Variant Cases of Creutzfeldt-Jakob Disease," Journal of Clinical Microbiology, Mar. 2005, vol. 43, No. 3, pp. 1118-1126.

Rao, Shobha S. et al., "Impaired Glucose Tolerance and Impaired Fasting Glucose," American Family Physician, Apr. 15, 2004, vol. 69, No. 8, pp. 1961-1968.

Yoshima, Hideo et al., "Comparative Study of the Carbohydrate Moieties of Rat and Human Plasma Alpha1-Acid Glycoproteins," The Journal of Biological Chemistry, Aug. 25, 1981, vol. 256, No. 16, pp. 8476-8484.

Adachi, Jun et al., "The Human Urinary Proteome Contains More Than 1500 Proteins, Including a Large Proportion of Membrane Proteins," Genome Biology, Sep. 1, 2006, vol. 7, R80-R80.16.

Sun, Wei et al., "Human Urine Proteome Analysis by Three Separation Approaches," Proteomics, 2005, vol. 5, pp. 4994-5001.

Tabares, Gloria et al., "Different Glycan Structures in Prostate-Specific Antigen from Prostate Cancer Sera in Relation to Seminal Plasma PSA," Glycobiology, 2006, vol. 16, No. 2, pp. 132-145.

Clark, M. F. et al., "Characteristics of the Microplate Method of Enzyme-Linked Immunosorbent Assay for the Detection of Plant Viruses," J. gen. Virol., 1977, vol. 34, pp. 475-483.

Nerurkar, Lata S. et al., "Rapid Detection of Herpes Simplex Virus in Clinical Specimens by Use of a Capture Biotin-Streptavidin Enzyme-Linked Immunosorbent Assay," Journal of Clinical Microbiology, Jul. 1984, vol. 20, No. 1, pp. 109-114.

Pickup, J.C. et al., "Is Type II Diabetes Mellitus a Disease of the Innate Immune System?," Diabetologia 1998, vol. 41, pp. 1241-1248.

Fernandez-Real, Jose Manuel et al., "Innate Immunity, Insulin Resistance and Type 2 Diabetes," Trends in Endocrinology and Metabolism, 2008, vol. 19, No. 1, pp. 10-16.

Davidson, Mayer B., "Clinical Irrelevance of the Current Diagnostic Criteria for Abnormal Carbohydrate Metabolism in Asymptomatic Individuals," Current Opinion in Endocrinology and Diabetes, 2005, vol. 12, pp. 437-443.

Wong, Tien Y. et al., "The Relationship of Fasting Glucose to Retinopathy: Re-visiting a Key Criterion Used to Diagnose Diabetes," Lancet, 2008, vol. 371(9614), pp. 736-743.

Gambino, Raymond, "Glucose: A Simple Molecule That is Not Simple to Quantify," Clinical Chemistry, 2007, vol. 53, No. 12, pp. 2040-2041.

Abdul-Ghani, Muhammad A. et al., "What is the Best Predictor of Future Type 2 Diabetes," Diabetes Care, Jun. 2007, vol. 30, No. 6, pp. 1544-1548.

Abdul-Ghani, Muhammad A. et al., "Contributions of Beta-Cell Dysfunction and Insulin Resistance to the Pathogenesis of Impaired Glucose Tolerance and Impaired Fasting Glucose," Diabetes Care, May 2006, vol. 29, No. 5, pp. 1130-1139.

Cali, Anna M. G. et al., "Metabolic Abnormalities Underlying the Different Prediabetic Phenotypes in Obese Adolescents," The Journal of Clinical Endocrinology & Metabolism, 2008, vol. 93, pp. 1767-1773.

Laakso, M. et al., "Insulin Sensitivity, Insulin Release and Glucagon-like Peptide-1 Levels in Persons with Impaired Fasting Glucoase and/or Impaired Glucose Tolerance in the EUGENE2 Study," Diabetologia, 2008, vol. 51, pp. 502-511.

Meyer, Christian et al., "Different Mechanisms for Impaired Fasting Glucose and Impaired Postprandial Glucose Tolerance in Humans," Diabetes Care, Aug. 2006, vol. 29, No. 8, pp. 1909-1914.

Abdul-Ghani, Muhammad A. et al., "Insulin Secretion and Action in Subjects with Impaired Fasting Glucose and Impaired Glucose Tolerance," Diabetes, May 2006, vol. 55, pp. 1430-1435.

Abdul-Ghani, Muhammad A., et al., "Risk of Progression to Type 2 Diabetes Based on Relationship Between Postload Plasma Glucose and Fasting Plasma Glucose," Diabetes Care, Jul. 2006, vol. 29, No. 7, pp. 1613-1618.

Wade, Andrew O. et al., "Glycaemic control in Critically Ill Patients with Cardiovascular Disease," Current Opinion in Critical Care, 2006, vol. 12, pp. 437-443.

Przybysz, Magdalena et al., "Relative Sialylation and Fucosylation of Synovial and Plasma Fibronectins in Relation to the Progression and Activity of Rheumatoid Arthritis," Glycoconj J, 2007, vol. 24, pp. 543-550.

Orczyk-Pawilowicz, Magdalena et al., "Alterations of N-Glycan Branching and Expression of Sialic Acid on Anmiotic Fluid Alpha-1-Acid Glycoprotein Derived From Second and Third Trimesters of Normal and Prolonged Pregnancies," Clinica Chimica Acta, 2006, vol. 367, pp. 86-92.

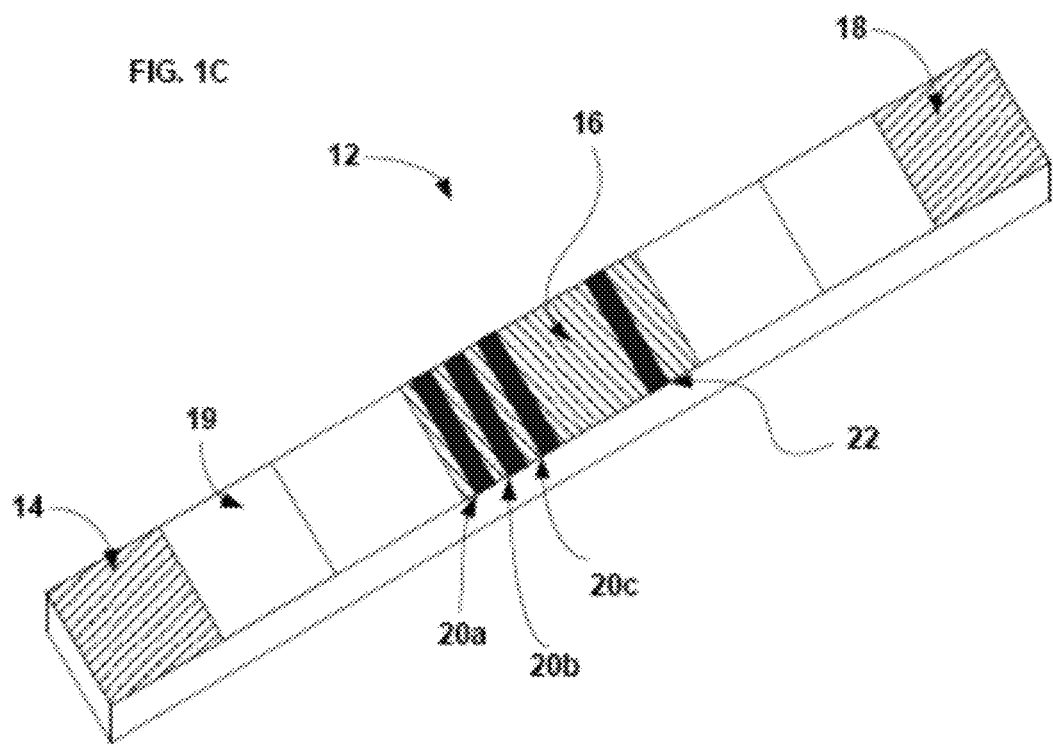

FIG. 3A
FIG. 3B
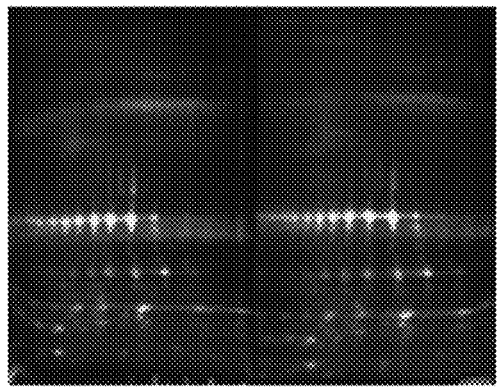
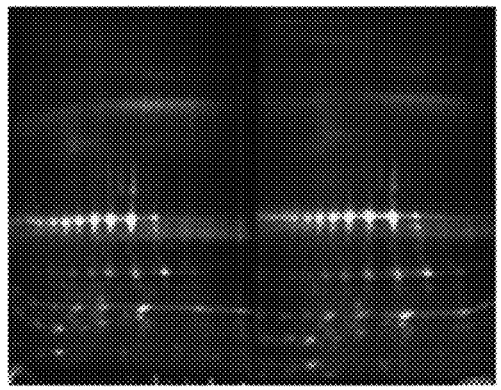
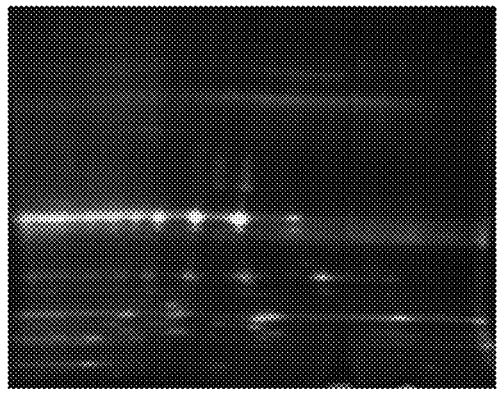
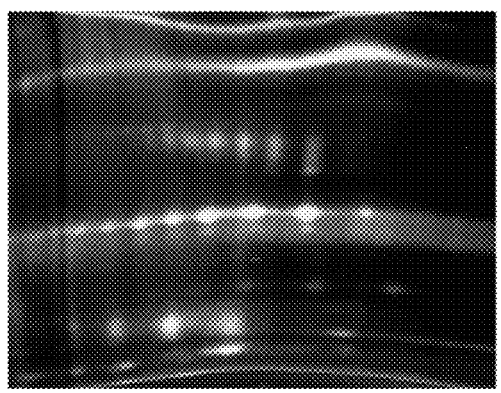
FIG. 3C
FIG. 3D

METHODS FOR DETECTING PRE-DIABETES AND DIABETES USING DIFFERENTIAL PROTEIN GLYCOSYLATION

CROSS REFERENCE TO RELATED APPLICATIONS

The present application claims priority to U.S. Provisional Patent Application No. 61/177,130, filed May 11, 2009, entitled "METHODS FOR DETECTING PRE-DIABETES AND DIABETES USING DIFFERENTIAL PROTEIN GLYCOSYLATION," the entire disclosure of which is hereby incorporated by reference in its entirety.

TECHNICAL FIELD

This relates to the field of diabetes, specifically to the identification of subjects who have pre-diabetes, diabetes, or diabetic complications.

BACKGROUND

Diabetes mellitus is a metabolic disorder characterized by chronic hyperglycemia with disturbances of carbohydrate, fat, and protein metabolism that result from defects in insulin secretion, insulin action, or both. Diabetes can present with characteristic symptoms such as thirst, polyuria, blurring of vision, chronic infections, slow wound healing, and weight loss. In its most severe forms, ketoacidosis or a non-ketotic hyperosmolar state may develop and lead to stupor, coma, and, in the absence of effective treatment, death.

Diabetes mellitus is subdivided into type 1 diabetes and type 2 diabetes. Type 1 diabetes (T1DM) results from autoimmune mediated destruction of the beta cells of the pancreas. Patients with T1DM exhibit little or no insulin secretion as manifested by low or undetectable levels of insulin or plasma C-peptide (also known in the art as "soluble C-peptide"). Type 2 diabetes (T2DM) is characterized by disorders of insulin action and insulin secretion, either of which may be the predominant feature. T2DM patients can be both insulin deficient and insulin resistant. At least initially, and often throughout their lifetime, these individuals do not need supplemental insulin treatment to survive. T2DM accounts for 90-95% of all cases of diabetes and can go undiagnosed for many years because the hyperglycemia is often not severe enough to provoke noticeable symptoms of diabetes or symptoms are simply not recognized. The majority of patients with T2DM are obese, and obesity itself may cause or aggravate insulin resistance. Many of those who are not obese by traditional weight criteria may have an increased percentage of body fat distributed predominantly in the abdominal region (visceral fat).

The symptoms of the early stages of diabetes often are not severe, not recognized, or may be absent. Consequently, hyperglycemia sufficient to cause pathological and functional changes may be present for a long time, occasionally up to ten years, before a diagnosis is made, usually by the detection of high levels of glucose in urine after overnight fasting during a routine medical work-up. The long-term effects of diabetes include progressive development of complications such as retinopathy with potential blindness, nephropathy that may lead to renal failure, neuropathy, microvascular changes, and autonomic dysfunction. People with diabetes are also at increased risk of cardiovascular, peripheral vascular, and cerebrovascular disease, as well as an increased risk of cancer. Several pathogenic processes are involved in the development of diabetes, including processes that destroy the insulin-secreting beta cells of the pancreas with consequent insulin deficiency, and changes in liver and smooth muscle cells that result in resistance to insulin uptake. The abnormalities of carbohydrate, fat, and protein metabolism are due to deficient action of insulin on target tissues resulting from insensitivity to insulin (insulin resistance) or lack of insulin (loss of beta cell function).

Over 18 million people in the United States have T2DM, and of these, about 5 million do not know they have the disease. These persons, who do not know they have the disease and who do not exhibit the classic symptoms of diabetes, present a major diagnostic and therapeutic challenge. Nearly 41 million persons in the United States are at significant risk of developing T2DM. These persons are broadly referred to as "pre-diabetic." As intervention early in the development of diabetes can substantially affect the long-term prognosis of the disease, it is beneficial to identify individuals who are pre-diabetic, or those subjects who will become diabetic.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 1C shows a perspective view of an example of a lateral flow test strip for the detection of multiple analytes, in accordance with various embodiments;

FIG. 3 is a series of digital images showing two-dimensional difference gel electrophoresis of saliva glycoproteins from patients with impaired glucose tolerance (IGT; FIG. 3A), impaired fasting glucose (IFG; FIG. 3B), type 2 diabetes mellitus (T2DM; FIG. 3C), or type 1 diabetes mellitus (T1DM; FIG. 3D) labeled with Cy5 (patient) or Cy3 (control) dyes, in accordance with various embodiments;

DETAILED DESCRIPTION OF DISCLOSED EMBODIMENTS

Figure 1A:
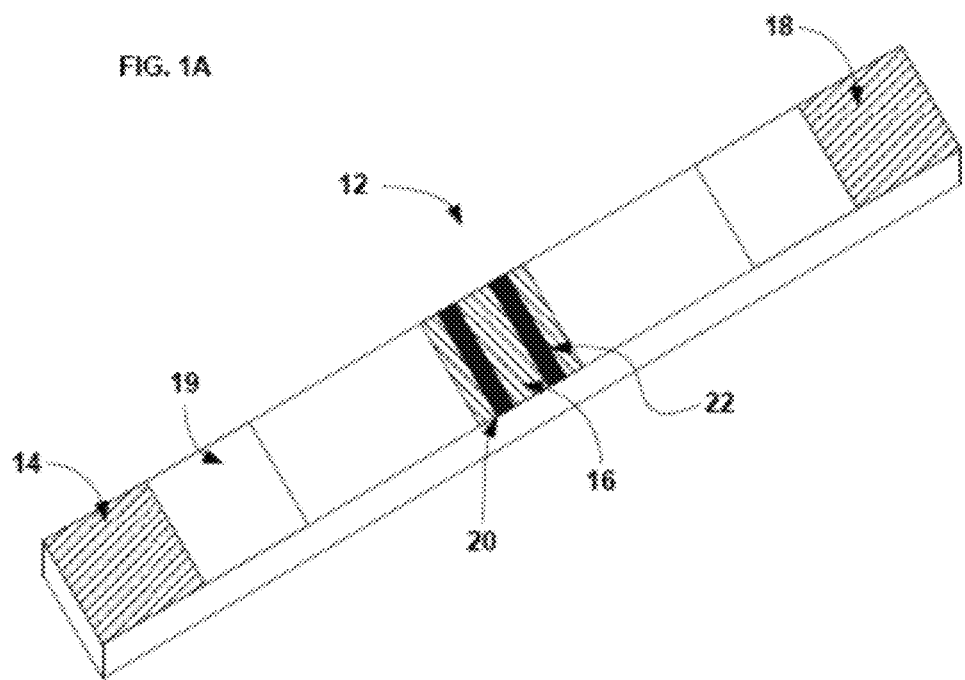
FIG. 1A is a perspective view of an example of a lateral flow test strip showing the basic components of the device and their relationship to each other, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

I. Introduction

The current screening for pre-diabetes includes measuring blood glucose levels during fasting conditions (to detect impaired fasting glucose; IFG) or following a glucose challenge (to determine impaired glucose tolerance; IGT). These tests aid in the assessment of potential risk for development of frank diabetes, such as type 2 diabetes mellitus (T2DM), and facilitates the institution of interventions to slow or prevent disease progression. The definition of IGT as a pre-diabetic condition was introduced many years ago to define disease risk based on oral glucose tolerance tests (OGTTs). Subsequently, the classification of IFG was introduced to provide a less complicated and less expensive parameter. IFG and IGT are now thought to reflect different aspects of the development of insulin resistance in T2DM, with differing underlying pathologies (Abdul-Ghani et al., *Diabetes Care* 29:1130-1139, 2006). Specifically, IGT is associated with peripheral insulin resistance and loss of first- and second-phase insulin secretion, while IFG is associated with hepatic insulin resistance and absence of first-phase insulin secretion. These distinctions in location of insulin resistance and extent of beta-cell dysfunction are consistently seen in Native American (Meyer et al., *Diabetes Care* 29:1909-1914, 2006), Mexican-American (Abdul-Ghani et al., *Diabetes* 55:1430-1435, 2006), and adult (Laakso et al., *Diabetologia* 51:502-511, 2008) and adolescent (Cali et al., *J. Clin. Endocrinol. Metab.* 93:1767-1773, 2008) Caucasian populations.

However, the use of blood glucose levels as a marker of pre-diabetes or frank diabetes has come under recent scrutiny. Specifically, the population-based studies upon which the current diagnostic criteria are based suffered from small sample size, inadequate knowledge of the glycemic history of the participants, and the inherently poor reproducibility of OGTTs (Davidson, *Curr. Opin. Endocrin. Diabet.* 12:437-443, 2005; Wong et al., *Lancet* 371:736-743, 2008). These findings raise serious questions about the adequacy and relevance of current diagnostic criteria for the diagnosis of T2DM. A separate, but related issue is the consistency of plasma glucose measurements themselves (Gambino, *Clin. Chem.* 53:2040-2041, 2007). Thus, these means of assessing pre-diabetes as well as overt T2DM are fraught with both technical and patient-variability issues.

Although levels of urinary glucose are also unreliable in assessing diabetic status, the evaluation of increased levels of protein in urine as well as detection of specific urinary proteins is useful for diagnosis of diabetic nephropathy and other diseases. More in-depth proteomic analysis of urine is expanding the list of possible urinary biomarkers of disease. Among the urine proteins identified by proteomics, glycoproteins constitute the largest fraction of the urine proteome characterized to date (Adachi et al., *Genome Biol.* 7:R80, 2006; Sun et al., *Proteomics* 5:4994-5001, 2005; Wang et al., *Mol. Cell. Proteomics* 5:560-562, 2006). The glycoproteome has been analyzed using Concanavalin A-captured glycoproteins from urine samples in healthy subjects and those with glomerular disease (Wang et al., *Mol. Cell. Proteomics* 5:560-562, 2006; Wang et al., *Biochem. Biophys. Res. Comm.* 371: 385-390, 3008). Glycoprotein biomarkers from cells and biological fluids such as serum and urine have been further characterized by analysis of the attached carbohydrate moieties in order to find a more specific or easily detectable molecular indicator. Examples include prostate specific antigen (Tabares et al., *Glycobiol.* 16:132-145, 2006), prion protein species (Pan et al., *J. Clin. Microbiol.* 43:1118-1126, 2005), fibronectin in rheumatoid synovial fluid (Przybysz et al., *Glycoconj. J.* 24:543-550, 2007), and alpha-1 acid glycoprotein (A1AG) in amniotic fluid (Orczyk-Pawilowicz et al., *Clin. Chem. Acta* 367:86-92, 2006).

Presented herein in various embodiments are direct lectin assays that may be used to detect changes in the glycosylation of biomolecules (glycosylation profile). In embodiments, changes in a glycosylation profile (such as glycosylation detected by one or more of PHA-E, LEL, DSL, ConA, AAL, or SNA) of a sample and/or a glycosylation pattern of one or more specific proteins (such as A1AG and A1AT) may be used to identify a subject as a pre-diabetic or a diabetic or as having a diabetic complication (such as diabetic nephropathy). In some examples, the subjects being tested may be diagnosed with IFG and/or IGT (compared to non-diabetic controls) and/or may have newly diagnosed type-2 diabetes. However, the method also may be used in detecting pre-diabetes or diabetes in subjects who have not been diagnosed with IFG and/or IGT.

Also presented herein in various embodiments are assays that may be used to determine the expression level and/or glycosylation pattern of specific proteins (such as A1AG or A1AT). The differences in the glycosylation profile of a plurality of biomolecules, and/or the expression or glycosylation pattern or amounts of specific proteins between these conditions may be used in the diagnosis of pre-diabetes and/or diabetes. In embodiments, devices that may be used for measuring the glycosylation profile are also disclosed.

II. Terms and Abbreviations

A1AG: alpha-1 acid glycoprotein
A1AT: alpha-1 antitrypsin
ALA: *Aleuria aurantia* lectin
ConA: Concanavalin A
DSL: *Datura stramonium* lectin
ECL: *Erythrina cristagalli* lectin
ELISA: enzyme-linked immunosorbent assay
GalNAc: N-acetyl galactosamine GlcNAc: N-acetyl glucosamine
GSL-2: *Griffonia simplicifolia* lectin II
HHL: *Hippeastrum hybrid* lectin
IFG: impaired fasting glucose
IGT: impaired glucose tolerance
LacNAc: N-acetyllactosamine
LEL: *Lycopersicon esculentum* lectin
LTL: *Lotus tetragonolobus* lectin
MAL: *Maackia amurensis* lectin I
LEL: *Lycopersicon esculentum* lectin
LTL: *Lotus tetragonolobus* lectin
NDM: newly diagnosed type-2 diabetes mellitus
NeuNAc: N-acetylneuraminic acid
OGTT: oral glucose tolerance test
PHA-E: *Phaseolus vulgaris* Agglutinin
SNA: *Sambucus nigra* lectin
T2DM: type 2 diabetes
VVL: *Vicia villosa* lectin Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Definitions and additional information known to one of skill in the art in immunology may be found, for example, in *Fundamental Immunology*, W. E. Paul, ed., fourth edition, Lippincott-Raven Publishers, 1999

In order to facilitate review of the various embodiments of this disclosure, the following explanations of specific terms are provided:

Alpha-1 acid glycoprotein (A1AG): An approximately 41-43 kDa protein which is one of the major acute phase proteins in humans, rats, mice and other species (also known as orosomucoid). The serum concentration of A1AG increases in response to systemic tissue injury, inflammation or infection, and is increased in renal complications (such as nephropathy). A1AG has five N-linked glycosylation sites of di-, tri-, and tetraantennary types, with at least twelve glycoforms detected in human plasma (Van Dijk et al., *Glyconj. J.* 12:227-233, 1995).

A1AG sequences are publicly available. For example, GenBank Accession number NC_000009.10 (116125157 . . . 116128578) discloses an exemplary human A1AG type 1 gene sequence (incorporated by reference as included in GenBank on May 11, 2009). GenBank Accession number NM_000607.2 and NP_000598.2 disclose exemplary human A1AG type 1 cDNA and protein sequences, respectively (both incorporated by reference as included in GenBank on May 11, 2009). GenBank Accession number NC_000009.10 (116131890 . . . 116135357) discloses an exemplary human A1AG type 2 gene sequence (incorporated by reference as included in GenBank on May 11, 2009). GenBank Accession number NM_000608.2 and NP_000599.1 disclose exemplary human A1AG type 2 cDNA and protein sequences, respectively (both incorporated by reference as included in GenBank on May 11, 2009). One skilled in the art will appreciate that A1AG nucleic acid and protein molecules may vary from those publicly available, such as A1AG sequences having one or more substitutions (for example conservative substitutions), deletions, insertions, or combinations thereof, while still retaining A1AG biological activity. In addition, A1AG molecules include fragments that retain the desired A1AG biological activity.

Alpha-1 antitrypsin (A1AT): Also known as alpha-1 proteinase inhibitor or Serpin A1. A 52 kDa serine protease inhibitor that is considered the most prominent serpin. The protein was called "antitrypsin" because of its ability to covalently bind and irreversibly inactivate the enzyme trypsin in vitro. The term alpha-1 refers to the enzyme's behavior on protein electrophoresis. There are several "clusters" of proteins in electrophoresis, the first being albumin, the second being the alpha, the third beta and the fourth gamma (immunoglobulins). The non-albumin proteins are referred to as globulins. The alpha region may be further divided into two sub-regions, termed "1" and "2". Alpha 1-antitrypsin is the main enzyme of the alpha-globulin 1 region.

A1AT sequences are publicly available. For example, GenBank Accession number NC_000014.7 discloses an exemplary human A1AT gene sequence (93914451 . . . 93926782) (incorporated by reference as included in GenBank on May 11, 2009). GenBank Accession numbers NM_001002235.2, NM_001002236.2, and NM_000295.4 disclose exemplary human A1AT cDNA sequences (each incorporated by reference as included in GenBank on May 11, 2009). GenBank Accession numbers NP_001002235.1, NP_001002236.1, and NP_000286.3 disclose exemplary human A1AT protein sequences (each incorporated by reference as included in GenBank on May 11, 2009). One skilled in the art will appreciate that A1AT nucleic acid and protein molecules may vary from those publicly available, such as A1AT sequences having one or more substitutions (for example conservative substitutions), deletions, insertions, or combinations thereof, while still retaining A1AT biological activity. In addition, A1AT molecules include fragments that retain the desired A1AT biological activity.

Analyte: An atom, molecule, group of molecules or compound of natural or synthetic origin (e.g., glycolipids or glycoproteins). An analyte sought to be detected or measured that is capable of binding specifically to a lectin in some embodiments described herein. Analytes may include, but are not limited to antibodies, drugs, hormones, antigens, haptens, glycoproteins, glycolipids, carbohydrates, apoproteins, or cofactors.

Antibody: A polypeptide ligand comprising at least a light chain or heavy chain immunoglobulin variable region which specifically binds an epitope of a protein listed in the tables below, or a fragment of any of these proteins. The term "specifically binds" refers to, with respect to an antigen such as the proteins listed in the tables below, the preferential association of an antibody or other ligand, in whole or part, with the protein. A specific binding agent binds substantially only to a defined target, such as protein of interest. A minor degree of non-specific interaction may occur between a molecule, such as a specific binding agent, and a non-target polypeptide. Specific binding may be distinguished as mediated through specific recognition of the antigen.

A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, *A Laboratory Manual*, Cold Spring Harbor Publications, New York (1988), for a description of immunoassay formats and conditions that may be used to determine specific immunoreactivity.

Antibodies may include a heavy chain and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W. H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Antigen: A chemical or biochemical compound, composition, structure, determinant, protein, glycoprotein or portion thereof that may stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Binding affinity: A term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the invention that these constants be measured or determined. Rather, affinities as used herein to describe interactions between molecules of the described methods and devices are generally apparent affinities (unless otherwise specified) observed in empirical studies, which may be used to compare the relative strength with which one molecule (e.g., an antibody or other specific binding partner, such as a lectin) will bind two other molecules (e.g., an analyte such as a glycoprotein). The concepts of binding affinity, association constant, and dissociation constant are well known.

Biological sample: Any biological sample obtained from a plant or animal subject. As used herein, biological samples include all clinical samples useful for detection of glycosylation profile, protein amount, or glycosylation pattern of proteins in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; mucus; saliva; milk; skin scrapes; surface washings; urine; sputum; sweat; semen; vaginal secretion; fluid from ulcers and/or other surface eruptions, blisters, abscesses, and/or extracts of tissues; cells or organs; cerebrospinal fluid; prostate fluid; pus; or bone marrow aspirates. The biological sample may also be a laboratory research sample such as a cell culture supernatant. In particular examples, the sample is urine, saliva, or serum. The sample is collected or obtained using methods well known to those skilled in the art.

Biomolecule: A molecule that is present in a biological sample including, but not limited to, proteins (such as polypeptides, proteins, or fragments thereof), lipids, and nucleic acids. The term "biomolecule" is specifically intended to cover naturally occurring biomolecules, as well as those which are recombinantly or synthetically produced. It should be noted that the term "biomolecule" includes modified forms of the biomolecules, such as glycosylated forms (for example, glycosylated proteins or peptides or glycosylated lipids).

Capture reagent: An unlabeled specific binding partner that is specific for (i) an analyte, as in a sandwich assay, or (ii) a detector reagent or an analyte, as in a competitive assay, or for (iii) an ancillary specific binding partner, which itself is specific for the analyte, as in an indirect assay. As used herein, an "ancillary specific binding partner" is a specific binding partner that binds to the specific binding partner of an analyte. For example, an ancillary specific binding partner may include an antibody specific for another antibody, for example, goat anti-human antibody. A "capture area" is a region of a lateral flow device where the capture reagent is immobilized. A lateral flow device may have more than one capture area, for example, a "primary capture area," a "secondary capture area," and so on. Often a different capture reagent will be immobilized in the primary, secondary, or other capture areas. Multiple capture areas may have any orientation with respect to each other on the lateral flow substrate; for example, a primary capture area may be distal or proximal to a secondary (or other) capture area and vice versa. Alternatively, a primary capture area and a secondary (or other) capture area may be oriented perpendicularly to each other such that the two (or more) capture areas form a cross or a plus sign or other symbol.

Contacting: "Contacting" includes in solution and solid phase, for example contacting a salivary sample, urinary sample or protein with a test agent. In one example, contacting includes contacting a sample with a lectin, such as those listed in Table 1 below. In another example, contacting includes contacting a sample with an antibody, for example contacting a sample that contains a protein of interest such as alpha-1 acid glycoprotein or alpha-1 antitrypsin.

Detecting or Detection: Refers to quantitatively or quantitatively determining the presence of the analyte(s) under investigation, such as a glycoprotein.

Detector reagent (or Detection reagent): A specific binding partner that is conjugated to a label.

Diabetes mellitus: A disease caused by a relative or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (sometimes referred to as "insulin-dependent diabetes" or "juvenile-onset diabetes") is an auto-immune disease characterized by destruction of the pancreatic β cells that leads to a total or near total lack of insulin. In type 2 diabetes (T2DM; sometimes referred to as "non-insulin-dependent diabetes" or "adult-onset diabetes"), the body does not respond to insulin, though it is present. As used herein, the term "metabolic condition" is used to refer to type 1 diabetes, type 2 diabetes, pre-diabetes, and diabetes complications.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W. B. Saunders Co., Philadelphia, 1992, 19$^{th}$ ed.).

The methods disclosed herein provide a means of identifying s subject who has diabetes or pre-diabetes, including both type 1 and type 2 diabetes. A "non-diabetic" or "normal" subject does not have any form of diabetes, such as type 1 diabetes, type 2 diabetes, or pre-diabetes.

Diabetic complication: Pathologies associated with diabetes that are secondary to uncontrolled carbohydrate metabolism of diabetes. Acute complications (such as hypoglycemia, ketoacidosis, or nonketotic hyperosmolar coma) may occur if the blood sugar is not adequately controlled. Chronic elevation of blood glucose level leads to damage of blood vessels (angiopathy) and chronic complications. In diabetes, the resulting chronic complications are grouped under "microvascular complications" (due to damage to small blood vessels) and "macrovascular complications" (due to damage to the arteries). Microvascular diabetic complications include diabetic nephropathy, diabetic retinopathy, diabetic neuropathy, and diabetic cardiomyopathy. Macrovascular complications lead to cardiovascular disease and include coronary artery disease, stroke, peripheral vascular disease, and diabetic myonecrosis. Additional chronic diabetic complications include diabetic foot, which results from a combination of diabetic neuropathy and peripheral vascular disease, and diabetic encephalopathy. In a particular example, the methods disclosed herein include diagnosis of one or more diabetic complication, such as microvascular complications, for example, diabetic nephropathy.

Glycosylation: Covalent modification of a biomolecule (such as a protein or lipid) with one or more oligosaccharide chains. Proteins having at least one oligosaccharide modification are referred to as "glycoproteins" or "glycosylated proteins." In the case of proteins, glycosylation is usually N-linked or O-linked. N-linked glycosylation refers to linkage of an oligosaccharide to the side chain amino group of an asparagine residue in a protein. O-linked glycosylation refers to linkage of an oligosaccharide to the hydroxyl side chain of a serine, threonine, or hydroxylysine amino acid in a protein.

The oligosaccharide chains of glycoproteins are enormously varied, due to the combination of various sugars (for example, N-acetylglucosamine, N-acetylgalactosamine, N-acetyllactosamine, mannose, galactose, glucose, N-acetylneuraminic acid, or fucose) and the presence of branched structures (such as biantennary, triantennary, or tetra-antennary structures).

Glycosylation profile: A representation of the glycosylation (such as the amount or type of glycosylation) of a plurality of biomolecules (such as a plurality of glycoproteins or glycolipids) in a biological sample, such as urine or saliva. The glycosylation profile provides information on the amount of one or more type of carbohydrate group (for example, N-acetylglucosamine, N-acetyl galactosamine, galactose, neuraminic acid, fructose, mannose, fucose, N-acetyllactosamine) or branch structure (such as bi-, tri-, or tetra-antennary) present on the plurality of biomolecules present in the sample. The glycosylation profile of a plurality of biomolecules in a sample may be determined by detecting of binding of biomolecules in the sample to one or more lectins. In some examples, the glycosylation profile of a sample from a subject is compared to the glycosylation profile of a reference in order to determine whether the subject has pre-diabetes, diabetes, or a diabetic complication.

Glycosylation pattern: The carbohydrate groups attached to a particular biomolecule (such as a particular glycoprotein or glycolipid), such as the number, structure, monosaccharide sequence, or location of the individual sugars on the biomolecule in a biological sample, such as urine or saliva. The glycosylation pattern of a biomolecule may be determined by detecting binding of the biomolecule to one or more lectins (such as by lectin-ELISA). In particular examples, the glycosylation pattern of a glycoprotein (such as A1AG or A1AT) in a sample from a subject is determined. In some examples, the glycosylation pattern of A1AG and/or A1AT in a sample from a subject is compared to the glycosylation pattern of A1AG and/or A1AT in a reference in order to determine whether the subject has pre-diabetes, diabetes, or a diabetic complication.

Immunoassay: A biochemical test that measures the presence or concentration of a substance in a sample, such as a biological sample, using the reaction of an antibody to its cognate antigen, for example the specific binding of an antibody to a protein. The presence of antigen and/or the amount of antigen present may be measured. For measuring proteins, for each antigen the presence and amount (abundance) of the protein may be determined or measured. The assay may be competitive or non-competitive.

Measuring the quantity of antigen (such as A1AG or A1AT) may be achieved by a variety of methods. One of the most common is to label either the antigen or antibody with a detectable label. Specific, non-limiting examples of labels include fluorescent tags, enzymatic linkages, and radioactive isotopes (for example $^{14}C$, $^{32}P$, $^{125}I$, and $^{3}H$ isotopes and the like). In some examples, an antibody that specifically binds one of an antigen of interest is labeled. Methods for labeling and guidance in the choice of labels appropriate for various purposes are discussed for example in Sambrook et al. (*Molecular Cloning: A Laboratory Manual*, Cold Spring Harbor, New York, 1989) Ausubel et al. (In Current Protocols in Molecular Biology, John Wiley & Sons, New York, 1998), and Harlow & Lane, (Antibodies, *A Laboratory Manual*, Cold Spring Harbor Publications, New York, 1988)).

Isolated: An isolated biological component (such as a nucleic acid, peptide or protein) has been substantially separated, produced apart from, or purified away from other biological components in the cell of the organism in which the component naturally occurs, for example the separation of a peptide from a sample, such as saliva, urine, serum or blood. Peptides and proteins that have been isolated include proteins purified by standard purification methods, such as chromatography, for example high performance liquid chromatography (HPLC) and the like. The term also embraces peptides, and proteins prepared by recombinant expression in a host cell as well as chemically synthesized peptide and nucleic acids. It is understood that the term "isolated" does not imply that the biological component is free of trace contamination, and may include molecules that are at least 50% isolated, such as at least 50%, 55%, 60%, 65%, 70%, 75%, 80%, 85%, 90%, 95%, 98%, 99%, or even 100% isolated.

Label: Any molecule or composition bound to an analyte, analyte analog, detector reagent, or binding partner that is detectable by spectroscopic, photochemical, biochemical, immunochemical, electrical, optical or chemical means. Examples of labels, including enzymes, colloidal gold particles, colored latex particles, have been disclosed (U.S. Pat. Nos. 4,275,149; 4,313,734; 4,373,932; and 4,954,452, each incorporated by reference herein). Additional examples of useful labels include, without limitation, radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulfur particles, protein-adsorbed tellurium particles, protein-adsorbed carbon particles, and protein-coupled dye sacs. The attachment of a compound (e.g., a detector reagent) to a label may be through covalent bonds, adsorption processes, hydrophobic and/or electrostatic bonds, as in chelates and the like, or combinations of these bonds and interactions and/or may involve a linking group.

In some examples, a label is conjugated directly or indirectly to another molecule, such as an antibody or a protein, to facilitate detection of that molecule. Specific, non-limiting examples of labels include fluorescent tags, enzymatic linkages, and radioactive isotopes (for example $^{14}C$, $^{32}P$, $^{125}I$, $^{3}H$ isotopes and the like). In some examples a lectin is labeled with a detectable marker, such as biotin. In some examples an antibody that specifically binds the lectin is labeled with a detectable marker, such as horseradish peroxidase. Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998), Harlow & Lane (Antibodies, *A Laboratory Manual*, Cold Spring Harbor Publications, New York, 1988).

Lateral flow device: A device that absorbs or adsorbs a liquid sample, routes that liquid sample to a detection zone, and uses antibody- or lectin-based detection methods to generate a visible signal in response to the presence or absence of a specific antigen (such as a protein or glycoprotein) or lectin-binding biomolecule (such as a glycoprotein or glycolipid). The device may be a test strip used in lateral flow chromatography, in which a test sample fluid, suspected of containing an analyte, flows (for example by capillary action) through the strip (which is frequently made of bibulous materials such as paper, nitrocellulose, and cellulose). The test fluid and any suspended analyte may flow along the strip to a detection zone in which the analyte (if present) interacts with a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,258,548; 6,555,390; 6,699,722; and 6,368,876; EP 0810436; and WO 92/12428; WO 94/01775; WO 95/16207; and WO 97/06439, each of which is incorporated by reference.

Many lateral flow devices are one-step lateral flow assays in which a biological fluid is placed in a sample area on a bibulous strip (though, non-bibulous materials may be used, and rendered bibulous by applying a surfactant to the material), and allowed to migrate along the strip until the liquid comes into contact with a specific binding partner (such as a lectin or antibody) that interacts with an analyte (such as a glycoprotein, glycolipid, or antigen) in the liquid. Once the analyte interacts with the binding partner, a signal (such as a fluorescent or otherwise visible dye) indicates that the interaction has occurred. Multiple discrete binding partners may be placed on the strip (for example in parallel lines) to detect multiple analytes in the liquid. The test strips may also incorporate control indicators, which provide a signal that the test has adequately been performed, even if a positive signal indicating the presence (or absence) of an analyte is not seen on the strip.

Lectin: A carbohydrate-binding protein, some of which are specific for one or more particular carbohydrate moieties. Most known lectins are multimeric, consisting of non-covalently associated subunits. A lectin may contain two or more of the same subunit, such as Concanavalin A (ConA), or different subunits, such as *Phaseolus vulgaris* agglutinin (PHA-E). In particular examples, lectins include *Aleuria aurantia* lectin (AAL), Concanavalin A (Con A), *Datura stramonium* lectin (DSL), *Erythrina cristagalli* lectin (ECL), *Griffonia simplicifolia* lectin II (GSL-2), *Hippeastrum hybrid* lectin (HHL), *Lycopersicon esculentum* lectin (LEL), *Lotus tetragonolobus* lectin (LTL), *Maackia amurensis* lectin I (MAL), *Phaseolus vulgaris* Agglutinin (PHA-E), *Sambucus nigra* lectin (SNA), and *Vicia villosa* lectin (VVL).

Linking group: A chemical arm between two compounds, for instance a compound and a label (e.g., an analyte, such as a glycoprotein or a glycolipid, and a label). To accomplish the requisite chemical structure, each of the reactants must contain a reactive group. Representative combinations of such groups are amino with carboxyl to form amide linkages; carboxy with hydroxy to form ester linkages or amino with alkyl halides to form alkylamino linkages; thiols with thiols to form disulfides; or thiols with maleimides or alkylhalides to form thioethers. Hydroxyl, carboxyl, amino and other functionalities, where not present in the native compound, may be introduced by known methods.

Likewise, a wide variety of linking groups may be employed. The structure of the linkage should be a stable covalent linkage formed to attach two compounds to each other (e.g., the label to the analyte). In some cases the linking group may be designed to be either hydrophilic or hydrophobic in order to enhance the desired binding characteristics, for instance of the modified ligand and its cognate receptor. The covalent linkages should be stable relative to the solution conditions to which linked compounds are subjected. Examples of linking groups will be from 1-20 carbons and 0-10 heteroatoms (NH, O, S) and may be branched or straight chain. Without limiting the foregoing, it should be obvious that only combinations of atoms that are chemically compatible comprise the linking group. For example, amide, ester, thioether, thiol ester, keto, hydroxyl, carboxyl, ether groups in combinations with carbon-carbon bonds are particular examples of chemically compatible linking groups.

Polypeptide: A polymer in which the monomers are amino acid residues which are joined together through amide bonds. When the amino acids are alpha-amino acids, either the L-optical isomer or the D-optical isomer may be used, the L-isomers being preferred. The terms "polypeptide" or "protein" or "peptide" as used herein are intended to encompass any amino acid sequence and include modified sequences such as glycoproteins. The term "polypeptide" or "protein" or "peptide" is specifically intended to cover naturally occurring proteins, as well as those which are produced by recombinant or synthetic methods.

Operable or contiguous contact: Two solid components are in operable contact when they are in contact, either directly or indirectly, in such a manner that an aqueous liquid may flow from one of the two components to the other substantially uninterruptedly, by capillarity or otherwise. Direct or contiguous contact means that the two elements are in physical contact, such as edge-to-edge or front-to-back. When two components are in direct contact, they may overlap with an overlap of about 0.5 mm to about 3 mm. However, the components may be placed with abutting edges. "Indirect contact" means that the two elements are not in physical contact, but are bridged by one or more conductors. Operable contact may also be referred to as "fluid transmitting" or "fluid continuous" contact.

Pre-diabetes: A condition identified in a subject by impaired glucose tolerance, alone or in combination with impaired fasting glucose regulation. An oral glucose tolerance test (OGTT) may be used to determine if a subject has impaired glucose tolerance (IGT). An OGTT two-hour plasma glucose of greater than or equal to 140 mg/dL and less than 200 mg/dL (7.8-11.0 mM) is considered to be IGT, and indicates that a subject has pre-diabetes. An OGTT of greater than or equal to 200 mg/dl indicates that a subject has frank diabetes, and an OGTT of less than 140 mg/dl indicates that a subject is normal (healthy) and does not have pre-diabetes or diabetes.

Generally, impaired fasting glucose (IFG) may also be used to identify a subject as pre-diabetic. Fasting plasma glucose (FPG) of greater than 100 mg/dL and less than 126 mg/dL (5.6-6.9 mM) indicates that a subject has IFG and has pre-diabetes. FPG of greater than or equal to 126 mg/dl indicates that a subject has frank diabetes, and an FPG of equal to or less than 100 mg/dl indices that subject is normal (healthy) and does not have pre-diabetes or diabetes.

Sample application area: An area where a fluid sample is introduced to a immunochromatographic test strip, such as an immunochromatographic test strip present in a lateral flow device. In one example, the sample may be introduced to the sample application area by external application, as with a dropper or other applicator. In another example, the sample application area may be directly immersed in the sample, such as when a test strip is dipped into a container holding a sample. In yet another example, the sample may be poured or expressed onto the sample application area.

Solid support (or substrate): Any material which is insoluble, or may be made insoluble by a subsequent reaction. Numerous and varied solid supports are known to those in the art and include, without limitation, nitrocellulose, the walls of wells of a reaction tray, multi-well plates, test tubes, polystyrene beads, magnetic beads, membranes, and microparticles (such as latex particles). Any suitable porous material with sufficient porosity to allow access by detector reagents and a suitable surface affinity to immobilize capture reagents (e.g., lectins or antibodies) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

It is contemplated that porous solid supports, such as nitrocellulose, described herein are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, may also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

The surface of a solid support may be activated by chemical processes that cause covalent linkage of an agent (e.g., a capture reagent) to the support. However, any other suitable method may be used for immobilizing an agent (e.g., a capture reagent) to a solid support including, without limitation, ionic interactions, hydrophobic interactions, covalent interactions and the like. The particular forces that result in immobilization of an agent on a solid phase are not important for the methods and devices described herein.

A solid phase may be chosen for its intrinsic ability to attract and immobilize an agent, such as a capture reagent. Alternatively, the solid phase may possess a factor that has the ability to attract and immobilize an agent, such as a capture reagent. The factor may include a charged substance that is oppositely charged with respect to, for example, the capture reagent itself or to a charged substance conjugated to the capture reagent. In another embodiment, a specific binding member may be immobilized upon the solid phase to immobilize its binding partner (e.g., a capture reagent). In this example, therefore, the specific binding member enables the indirect binding of the capture reagent to a solid phase material.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

A "lateral flow substrate" is any solid support or substrate that is useful in a lateral flow device.

Specific binding partner (or binding partner): A member of a pair of molecules that interact by means of specific, noncovalent interactions that depend on the three-dimensional structures of the molecules involved. Typical pairs of specific binding partners include antigen/antibody, carbohydrate/lectin, hapten/antibody, hormone/receptor, nucleic acid strand/ complementary nucleic acid strand, substrate/enzyme, inhibitor/enzyme, biotin/(strept)avidin, and virus/cellular receptor.

The phrase "specifically binds to an analyte" or "specifically immunoreactive with," refers to a binding reaction which is determinative of the presence of the analyte in the presence of a heterogeneous population of molecules such as proteins and other biologic molecules. Thus, under designated assay conditions, the lectins or antibodies bind to a particular analyte, such as proteins, glycoproteins and/or glycolipids, and do not bind in a significant amount to other analytes present in the sample. A variety of assay formats may be used to select lectins or antibodies specifically reactive with a particular analyte, such as a glycoprotein or glycolipid or a particular protein. For example, solid-phase ELISA immunoassays are routinely used to select monoclonal antibodies specifically immunoreactive with a protein. See Harlow and Lane, *Antibodies, A Laboratory Manual*, CSHP, New York (1988), for a description of immunoassay formats and conditions that may be used to determine specific immunoreactivity.

Subject: Living multi-cellular vertebrate organisms, a category that includes human and non-human mammals (such as laboratory or veterinary subjects).

Substantially the same: An amount that is not significantly different from a reference or control. This may be measure quantitatively, such as by using statistical methods, for example a Student's T-test or ANOVA. For example, a glycosylation profile of a sample from a subject is substantially the same as a glycosylation profile of a sample from a control subject when the amount of glycosylation detected by one or more lectins is not different between the two samples.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein may be used in the practice or testing of this disclosure, suitable methods and materials are described below. The term "comprises" means "includes." All publications, patent applications, patents, and other references mentioned herein are incorporated by reference in their entirety. All GenBank Accession Nos. mentioned herein are incorporated by reference in their entirety. In case of conflict, the present specification, including explanations of terms, will control. In addition, the materials, methods, and examples are illustrative only and not intended to be limiting.

III. Methods for Identifying a Subject with Pre-diabetes or Diabetes

In various embodiments, methods are disclosed herein that may be of use to determine whether a subject has a diabetic condition, for instance pre-diabetes or diabetes. In some embodiments, these methods may utilize a biological sample (such as urine, saliva, blood, serum, amniotic fluid, or tears, for example, saliva, urine, or serum), for the detection of a glycosylation profile of a plurality of biomolecules (such as glycoproteins or glycolipids) in the sample. In other embodiments, the glycosylation pattern of one or more specific proteins (such as A1AG or A1AT) may also be used to determine if a subject has a diabetic condition, such as pre-diabetes or diabetes. In some examples, the methods also may include utilizing a biological sample (for example urine or saliva) for determining the amount of one or more proteins, including, but not limited to, A1AG or A1AT. In additional examples, the methods also may include determining the glycosylation pattern of A1AG or A1AT.

A. Glycosylation Profile

In some embodiments, the methods disclosed herein may include determining a glycosylation profile (such as the amount or type of glycosylation of a plurality of biomolecules) of a biological sample (such as a biological fluid, for example, urine or saliva). In embodiments, a change in the glycosylation profile of a sample may reflect a change in the amount or type of glycosylation (such as N-glycosylation) of a particular biomolecule(s) as compared to the amount or type of the particular biomolecule(s) in a reference standard, such as a reference sample or quantity. A change in the glycosylation profile may also reflect the presence of glycosylation (such as N-glycosylation) of a particular biomolecule(s) that is not present on the particular biomolecule(s) in a reference, or the absence of glycosylation (such as N-glycosylation) of a particular biomolecule(s) that is present on the particular biomolecule(s) in a reference. Thus, in various embodiments, the glycosylation profile may not provide information about modification of any one specific biomolecule in the sample, but may provide information about the amount or type of glycosylation (such as N-glycosylation) present on any biomolecule present in the sample or on a population of biomolecules in the sample.

In some embodiments, the glycosylation profile of a sample is determined by measuring the binding of biomolecules in a biological sample to one or more lectins. In various embodiments, lectins may bind specifically to particular carbohydrates or oligosaccharide structures, such as those present in glycoproteins or glycolipids (see, e.g., Section V). In some examples, a biological sample (such as urine, saliva, or serum) which contains a plurality of biomolecules may be contacted with one or more lectins, and binding of biomolecule(s) to the lectin(s) is detected. In various embodiments, the amount of biomolecule(s) binding to a lectin having a particular specificity indicates the amount of that particular type of glycosylation present on the plurality of biomolecule(s) in the sample.

In some embodiments, the method includes comparing a glycosylation profile of a test sample (such as urine, saliva, or serum) from a subject of interest with a glycosylation profile of a reference standard, such as a reference sample or quantity. In one embodiment, the method may determine whether the subject has pre-diabetes or diabetes. In embodiments, if the reference is a normal reference and the glycosylation profile of the test sample is substantially the same as the glycosylation profile of the reference (for example, the amount or type of glycosylation is substantially the same), the subject is determined not to have pre-diabetes or diabetes, respectively. However, in embodiments, if the glycosylation profile of the test sample is changed relative to the glycosylation profile of the reference (for example, the amount or type of glycosylation is increased), the subject is determined to have pre-diabetes or diabetes, respectively.

In another embodiment, if the reference is a pre-diabetes or diabetes reference and the glycosylation profile of the test sample is substantially the same as the reference sample (for example the amount or type of glycosylation is essentially the same, such as not significantly different), then the subject may be determined to have pre-diabetes or diabetes, respectively. In embodiments, of the glycosylation profile of the test sample is changed (for example, a decrease in the amount or type of glycosylation) relative to the reference, the subject is determined not to have pre-diabetes or diabetes, respectively.

In particular examples, the method may include detecting an increase, such as at least about a 2, 3, 4, 5, 6, 7, 8, 9, 10, 12, 15, or 20-fold increase (for example about a 2-fold to 20-fold, 3-fold to 15-fold, or 5-fold to 10-fold increase), in at least one informative parameter of the glycosylation profile, such as the amount of one or more type of glycosylation (such as N-glycosylation, for example, one or more carbohydrate group, such as N-acetylglucosamine, N-acetylgalactosamine, N-acetyllactosamine, N-acetylneuraminic acid, mannose, fucose, or galactose), or the amount of one or more oligosaccharide structures (such as a bi-antennary, tri-antennary, or tetra-antennary structure) present in a sample. An "informative parameter" refers to a measure (such as a quantity of biomolecule binding to a particular lectin) that detects a type of glycosylation associated with pre-diabetes or diabetes.

In particular examples, the amount of glycosylation may be detected by determining an amount of a sample binding to a lectin (such as PHA-E, LEL, DSL, ConA, AAL, SNA, or MAL). In some examples, the method may include detecting an increase in biomolecule glycosylation recognized by the lectin PHA-E (such as at least about a 2, 3, 4, or 5-fold increase, for example about a 2-fold or 3-fold increase), such as lactosamine glycosylation (for example, Gal-$\beta$1,4 GlcNAc), in a subject with pre-diabetes or diabetes. In additional examples, the method may include detecting an increase in biomolecule glycosylation recognized by the lectin LEL (such as at least about a 2, 3, 4, or 5-fold increase, for example about a 2-fold or 3-fold increase), such as trimers or tetramers of GlcNAc, in a subject with pre-diabetes or diabetes. In additional examples, the method may include detecting an increase in biomolecule glycosylation recognized by the lectin AAL (such as at least about a 2, 3, 4, or 5-fold increase, for example about a 2-fold or 3-fold increase), such as fucose, in a subject with pre-diabetes or diabetes.

In further examples, the method may include detecting an increase in biomolecule glycosylation recognized by the lectin DSL (such as at least about a 2, 3, 4, or 5-fold increase, for example about a 2-fold or 3-fold increase) in a subject with pre-diabetes or diabetes. In additional examples, the method may include detecting an increase in biomolecule glycosylation recognized by the lectin ConA (such as at least about a 2-fold to 20-fold increase, for example about a 2-fold, 5-fold, 10-fold, 15-fold, or 20-fold increase) in a subject with pre-diabetes or diabetes. In still further examples, the method may include detecting an increase in biomolecule glycosylation recognized by the lectin SNA (such as at least about a 2-fold to 15-fold increase, for example about a 2-fold, 5-fold, 10-fold, or 15-fold increase) in a subject with pre-diabetes or diabetes. In some examples, a glycosylation profile may include the amount of sample binding to PHA-E, LEL, AAL, DSL, ConA, SNA, MAL, or a combination of two or more thereof.

In still further examples, the amount of the increase of glycosylation detected by sample binding to a lectin (such as ConA or SNA) may be useful to differentiate whether a subject has pre-diabetes or diabetes. For example, an increase in sample binding to ConA of about 2-fold to 8-fold (such as about 2-fold, 3-fold, 4-fold, 5-fold, 6-fold, 7-fold, or 8-fold) may indicate that the subject has pre-diabetes, while an increase in sample binding to ConA of about 10-fold to 20-fold (such as about 10-fold, 12-fold, 15-fold, 18-fold, or 20-fold) may indicate that the subject has diabetes. In another example, an increase in sample binding to SNA of about 2-fold to about 5-fold (such as about 2-fold, 3-fold, 4-fold, or 5-fold) may indicate that the subject has pre-diabetes, while an increase in sample binding to SNA of about 8-fold to about 15-fold (such as about 8-fold, 9-fold, 10-fold, 12-fold, or 15-fold) may indicate that the subject has diabetes.

In an additional embodiment, the method may include detecting an increase in a ratio of sample binding to two lectins, such as a test lectin and a reference lectin. In some examples the test lectin may include SNA or ConA, while the reference lectin may include MAL or ECL. In particular examples, an increase in the ratio of SNA binding to MAL binding by a sample (such as an increase of about 2-fold to about 20-fold) compared to a normal reference standard, such as a reference sample or quantity, may indicate that the subject has pre-diabetes or diabetes. In additional examples, an increase in the ratio of SNA binding to MAL binding of about 2-fold to 5-fold (for example, about 2-fold, 3-fold, 4-fold, or 5-fold) compared to a normal reference standard may indicate that the subject has pre-diabetes. In other examples, an increase in the ratio of SNA binding to MAL binding of about 10-fold to 15-fold (for example, about 10-fold, 11-fold, 12-fold, 13-fold, 14-fold, or 15-fold) compared to a normal reference standard may indicate that the subject has diabetes.

In further examples, an increase in the ratio of ConA binding to MAL binding by a sample (such as an increase of about 2-fold to about 20-fold) compared to a normal reference standard, such as a reference sample or quantity, may indicate that the subject has pre-diabetes or diabetes. In some examples, an increase in the ratio of ConA binding to MAL binding of about 3-fold to 8-fold (for example, about 3-fold, 4-fold, 5-fold, 6-fold, 7-fold, or 8-fold) compared to a normal reference standard may indicate that the subject has pre-diabetes. In other examples, an increase in the ratio of ConA binding to MAL binding of about 12-fold to 20-fold (for example, about 12-fold, 13-fold, 14-fold, 15-fold, 16-fold, 17-fold, 18-fold, 19-fold, or 20-fold) compared to a normal reference standard may indicate that the subject has diabetes.

Of course, it is not necessary to compare biomolecule glycosylation of a sample directly to glycosylation of another sample. Reference standards (such as known quantitative amounts of glycosylation) may be used in lieu of direct comparison to results from a reference sample. Hence, in embodiments, the comparison may be made to a reference (which is understood to be results from an actual sample or population of samples, or a qualitative or quantitative reference that represents a cut-off value, such as a diagnostic or prognostic level of glycosylation).

B. Amount and Glycosylation of Specific Proteins

In some embodiments, the methods disclosed herein also may include determining an amount of one or more proteins present in a biological sample (such as urine or saliva), such as proteins associated with pre-diabetes or diabetes. In various embodiments, the methods may include comparing an amount of one or more proteins in a test sample (such as urine or saliva) from a subject of interest with an amount of said protein in a reference standard, such as a reference sample or quantity. In embodiments, if the reference is a normal reference, and the amount of one or more protein in the test sample is substantially the same as the amount of said protein in the reference, the subject may be determined not to have pre-diabetes or diabetes. However, if the amount of one or more protein of the test sample is changed relative to the amount of said protein of the reference, the subject may be determined to have pre-diabetes or diabetes.

In another embodiment, if the reference is a pre-diabetes or diabetes reference, and the amount of one or more protein in the test sample is substantially the same as the amount of said protein in the reference, then the subject may be determined to have pre-diabetes or diabetes, respectively. If the amount of one or more protein in the test sample is changed relative to the reference, the subject may be determined not to have pre-diabetes or diabetes, respectively. Hence, the amount of one or more protein may provide an additional diagnostic criterion for these disorders.

In some examples, the method may include detecting an increase, such as at least a 2-fold to 10-fold increase (such as at least about a 2, 3, 4, 5, 6, 8, or 10-fold increase) in the amount of one or more proteins present in a biological sample. In particular examples, the method may include detecting an increase in the amount of A1AG and/or A1AT protein in a sample from a subject with pre-diabetes or diabetes, as compared to a control sample. In additional examples, the method may include detecting an increase or decrease, such as at least a 2, 3, 4, or 5-fold increase or decrease, in the ratio of the amount of A1AG to A1AT in the sample. In particular examples, the ratio of A1AG to A1AT in a sample from a subject with diabetes may be decreased (such as about a 2-fold to 5-fold decrease, for example about a 2-fold to 3-fold decrease) compared to a control sample.

In yet another embodiment, the methods disclosed herein also may include determining the glycosylation pattern of one or more particular proteins (such as proteins associated with pre-diabetes or diabetes, for example A1AG or A1AT) in a biological sample. The glycosylation pattern of a protein may be determined by detecting binding of the protein to one or more lectins. In some embodiments, the glycosylation pattern of a protein may be determined by measuring the binding of the protein in a biological sample to one or more lectins, such as lectins that detect a type of glycosylation of the protein that has been found to be associated with pre-diabetes or diabetes. The presence (or change, such as increase or decrease) of one or more particular types of glycosylation as detected by binding to a lectin specific for type of glycosylation on the protein may be the glycosylation pattern of the protein in this example.

In some embodiments, the method may include comparing a glycosylation pattern of one or more proteins in a test sample (such as urine or saliva) from a subject of interest with a glycosylation pattern of said proteins from a reference standard, such as a reference sample or quantity. In various embodiments, if the reference is a normal reference and the glycosylation pattern of one or more protein of the test sample is substantially the same as the glycosylation pattern of said protein of the reference, the subject may be determined not to have pre-diabetes or diabetes. However, if the glycosylation pattern of one or more protein of the test sample is changed relative to the glycosylation pattern of said protein of the reference, the subject may be determined to have pre-diabetes or diabetes.

In another embodiment, if the reference is a pre-diabetes or diabetes reference, and the glycosylation pattern of one or more proteins in the test sample is substantially the same as the glycosylation pattern of said proteins in the reference, then the subject may be determined to have pre-diabetes or diabetes, respectively. In embodiments, if the glycosylation pattern of one or more protein in the test sample is changed relative to the reference, the subject may be determined not to have pre-diabetes or diabetes, respectively.

In some examples, the method may include detecting an increase, such as at least a 2, 3, 4, or 5 fold increase, in the amount or type of glycosylation of one or more proteins present in the sample. In a particular example, the method may include detecting an increase (such as at least about a 2, 3, 4, or 5-fold increase, for example about a 2-fold or 3-fold increase) in the amount of glycosylated A1AG recognized by the lectin ConA in the sample in a subject with pre-diabetes. In another particular example, the method may include detecting an increase in the amount of glycosylated A1AG recognized by the lectin SNA (such as at least about a 2, 3, 4, or 5-fold increase, for example about a 2-fold or 3-fold increase) in the sample in a subject with pre-diabetes. In an additional example, the method may include detecting an increase in the amount of glycosylated A1AG recognized by the lectin AAL (such as at least about a 2, 3, 4, or 5-fold increase, for example about a 2-fold or 3-fold increase) in the sample in a subject with diabetes. Thus, in some examples, the glycosylation pattern of A1AG may include the amount of A1AG binding to particular lectins (such as ConA, SNA, AAL, or a combination of two or more thereof).

Of course, it may not be not necessary to compare the amount of one or more proteins associated with pre-diabetes or diabetes of a sample directly to the amount of the proteins of another sample. Likewise, it may not be necessary to compare the glycosylation pattern of a protein associated with pre-diabetes or diabetes directly to the glycosylation pattern of the protein of another sample. Reference standards (such as known quantitative amounts of glycosylation or a particular protein) may be used in various embodiments in lieu of direct comparison to results from a reference sample. Hence, the comparison may be made to a normal reference (which may be understood to be results from an actual sample or population of samples, or a qualitative or quantitative reference that represents a cut-off value, such as a diagnostic or prognostic level of glycosylation or a particular protein).

In additional embodiments, the glycosylation profile of a sample from a subject may be determined, and the amount and/or glycosylation pattern of one or more particular proteins may be determined (such as sequentially or simultaneously). In one example, the glycosylation profile and the amount of one or more proteins may be determined in a sample from a subject. In another example, the glycosylation profile and the glycosylation pattern of one or more proteins may be determined in a sample from a subject. In a further example, the glycosylation profile, and the amount and glycosylation pattern of one or more proteins may be determined in a sample from a subject.

IV. Methods for Identifying a Subject with Diabetic Complications

In another embodiment, the method may be a method to determine if a subject has a diabetic complication. In particular examples, the diabetic complication may be a chronic complication. Chronic elevation of blood glucose level leads to damage of blood vessels (angiopathy) and chronic diabetic complications. The resulting chronic complications are grouped as "microvascular complications" (due to damage to small blood vessels) and "macrovascular complications" (due to damage to the arteries).

Microvascular diabetic complications include (but are not limited to) diabetic nephropathy (such as damage to the kidney which may lead to chronic renal failure), diabetic retinopathy (such as growth of friable, poor-quality blood vessels in the retina which may lead to vision loss), diabetic neuropathy (such as abnormal and decreased sensation, usually in a "glove and stocking" distribution), and diabetic cardiomyopathy (damage to the heart leading to diastolic dysfunction and eventually heart failure).

Macrovascular complications may lead to cardiovascular disease, to which accelerated atherosclerosis may be a contributor. Macrovascular complications include (but are not limited to) coronary artery disease (such as angina or myocardial infarction), stroke, peripheral vascular disease, and diabetic myonecrosis (which may lead to muscle wasting).

Additional diabetic complications may include "diabetic foot" which may lead to skin ulcers, infection, necrosis, and/or gangrene. This complication may be due to a combination of diabetic neuropathy (such as numbness or insensitivity) and vascular damage. Diabetic encephalopathy (such as cognitive decline or dementia) is another diabetic complication.

The methods described herein include methods to determine whether a subject has one or more diabetic complications. In some embodiments, the method may include detecting an increase (such as at least about a 5-fold increase to about 100-fold increase, for example, about a 5-fold, 10-fold, 25-fold, 50-fold, 60-fold, or 100-fold increase) in the glycosylation profile, such as the amount of one or more types of glycosylation (for example, one or more carbohydrate groups, such as N-acetylglucosamine, N-acetylgalactosamine, N-acetyllactosamine, N-acetylneuraminic acid, mannose, fucose, or galactose) or an amount of one or more oligosaccharide structures (such as a bi-antennary, tri-antennary, or tetra-antennary structure) present in a sample. In some embodiments, the method may include comparing a glycosylation profile of a test sample (such as urine or saliva) from a subject of interest with a glycosylation profile of a reference standard, such as a reference sample or quantity. In some examples, the method may include detecting an increase in glycosylation recognized by the lectin AAL (such as at least about 20-fold to 100-fold increase, for example, about a 25-fold, 50-fold, 60-fold, or 100-fold increase), such as mannose, in a subject with a diabetic complication. In additional examples, the method may include detecting an increase in glycosylation recognized by the lectin SNA (such as at least about a 20-fold to 100-fold increase, for example, about a 25-fold, 50-fold, 60-fold, or 100-fold increase), such as N-acetylneuraminic acid, in a subject with a diabetic complication.

In one embodiment, if the reference is a normal reference, and the glycosylation profile of the test sample is substantially the same as the glycosylation profile of the normal sample or reference (for example, the amount or type of glycosylation is substantially the same), the subject may be determined not to have a diabetic complication. However, if the glycosylation profile of the test sample is changed relative to the glycosylation profile of the normal sample or reference (for example, the amount of one or more type of glycosylation is increased), the subject may be determined to have a diabetic complication. In a particular example, the diabetic complication may be a microvascular complication, for example, diabetic nephropathy, diabetic retinopathy, or diabetic neuropathy.

In another embodiment, if the reference is a diabetic complication reference, and the glycosylation profile of the test sample is substantially the same as the reference (for example the amount or type of glycosylation is essentially the same, such as not significantly different), then the subject may be determined to have a diabetic complication. If the glycosylation profile of the test sample is changed (for example, a decrease in the amount or type of glycosylation) relative to the reference, then the subject may be determined not to have a diabetic complication.

In additional examples, the method for identifying a subject as having a diabetic complication may include determining the amount of one or more proteins (such as proteins associated with diabetic complication, such as A1AG or A1AT) in a sample from the subject. In embodiments, the methods may include comparing an amount of one or more proteins in a test sample (such as urine or saliva) from a subject of interest with an amount of said protein from a reference standard, such as a reference sample or quantity. In particular examples, the method may include detecting an increase in protein amount (such as at least about a 20-fold increase to about 1000-fold increase, such as about a 20-fold, 50-fold, 70-fold, 100-fold, 300-fold, 500-fold, or 1000-fold increase) in a subject with a diabetic complication compared to a reference standard, such as a reference sample or quantity. In additional examples, the method may include detecting an increase or decrease, such as at least a 2, 3, 4, or 5-fold increase or decrease, in the ratio of the amount of A1AG to A1AT in the sample. In particular examples, the ratio of A1AG to A1AT in a sample from a subject with a diabetic complication may be decreased (such as about a 2-fold or 3-fold decrease) compared to a reference standard, such as a reference sample or quantity.

In various embodiments, if the reference is a normal reference, and the amount of one or more proteins of the test sample is substantially the same as the amount of said protein in the normal sample, the subject may be determined not to have a diabetic complication. However, if the amount of one or more proteins of the test sample is changed relative to the amount of said protein of the normal sample or standard, the subject is determined to have a diabetic complication.

In another embodiment, if the reference is a diabetic complication reference, and the amount of one or more protein in the test sample is substantially the same as the amount of said protein in the reference, then the subject may be determined to have a diabetic complication. If the amount of one or more proteins in the test sample is changed relative to the reference, the subject is determined not to have a diabetic complication.

In additional embodiments, the glycosylation profile of a sample from a subject may be determined, and the amount and/or glycosylation pattern of one or more particular proteins may be determined (such as sequentially or simultaneously). In one example, the glycosylation profile and the amount of one or more proteins may be determined in a sample from a subject. In another example, the glycosylation profile and the glycosylation pattern of one or more proteins may be determined in a sample from a subject. In a further example, the glycosylation profile, and the amount and glycosylation pattern of one or more proteins may be determined in a sample from a subject.

V. Monitoring

In another embodiment, the method may be a method to determine whether a therapy is effective for the treatment of the subject. Thus, in various embodiments, the method may be performed multiple times over a specified time period, such as days, weeks, months or years. The diagnostic methods described herein are valuable tools for practicing physicians to make quick treatment decisions for diabetic conditions, including pre-diabetes and diabetes. These treatment decisions may include the decision to administration of an anti-diabetic agent, and/or the decision to monitor a subject for the onset and/or advancement of diabetes. The treatment decisions may also include lifestyle monitoring. The method disclosed herein may also be used to monitor the effectiveness of a therapy.

In various embodiments, the glycosylation profile, protein expression level, or glycosylation pattern of a sample from a subject may be assessed as described above and compared to a reference. If the reference, such as a reference sample or quantity, is a normal reference, and the glycosylation profile (or amount or glycosylation pattern of a particular protein) of the test sample is substantially the same as the glycosylation profile (or amount or glycosylation pattern of a particular protein) of the normal reference, the subject may be determined to have an effective therapy Conversely, if the glycosylation profile (or amount or glycosylation pattern of a particular protein) of the test sample is different from the glycosylation profile (or amount or glycosylation pattern of a particular protein) of the normal reference, the subject may be determined to have an ineffective therapy. In embodiments, if the reference standard, such as a reference sample or quantity, is a pre-diabetes or diabetes reference, and the glycosylation profile (or amount or glycosylation pattern of a particular protein) does not differ from the reference, then the subject may be determined to have an ineffective therapy. Conversely, if the glycosylation profile (or amount or glycosylation pattern of a particular protein) of the test sample is different from the reference, the subject may be determined to have an effective therapy.

Following the assessment of the glycosylation profile, protein expression level, or glycosylation pattern identified herein, the assay results, findings, diagnoses, predictions and/or treatment recommendations may be recorded and/or communicated to technicians, physicians and/or patients, for example. In certain embodiments, computers may be used to communicate such information to interested parties, such as patients and/or the attending physicians. In various embodiments, based on the measurement, the therapy administered to a subject may be modified.

In one embodiment, a diagnosis, prediction and/or treatment recommendation based on the glycosylation profile, protein expression level, or glycosylation pattern in a test subject of one or more of the glycosylated biomolecules described herein may be communicated to the subject as soon as possible after the assay is completed and the diagnosis and/or prediction is generated. In some embodiments, the results and/or related information may be communicated to the subject by the subject's treating physician. Alternatively, the results may be communicated directly to a test subject by any means of communication, including writing, such as by providing a written report, electronic forms of communication, such as email, or telephone. In embodiments, communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present methods are not limited to methods which utilize this particular communications system. In certain embodiments of the methods, all or some of the method steps, including the assaying of samples, diagnosing of diseases, and communicating of assay results or diagnoses, may be carried out in diverse (e.g., foreign) jurisdictions.

In several embodiments, identification of a subject as being pre-diabetic or diabetic may result in the physician treating the subject, such as by prescribing an anti-hyperglycemic or an anti-diabetic agent to inhibit or delay the onset or progression of type II diabetes. In additional embodiments, the dose or dosing regimen may be modified based on the information obtained using the methods disclosed herein. In some embodiments, the anti-diabetic agent may contain a biguanide of the formula:

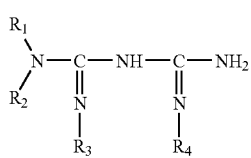

Formula 1 wherein $R_1$ and $R_2$ are independently selected from alkyl, lower alkyl, alkenyl, lower alkenyl, cycloalkyl, aryl, or an arylalkyl of the formula:

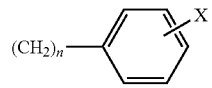

Formula 2 wherein X is hydrogen or halogen and n=0, 1 or 2; $R_3$ and $R_4$ are independently selected from hydrogen, alkyl, lower alkyl, alkenyl, lower alkenyl, cycloalkyl, alkoxy, lower alkoxy, alkoxyalkyl; and pharmaceutically acceptable salts thereof. In particular embodiments, the biguanide antidiabetic agent may be metformin. Metformin may be manufactured by Lyonnaise Industrielle Pharmaceutique SA (Lyons, France), and is also known by its acronym LIPHA SA, and may be commercially distributed in the United States as a hydrochloride salt by the Bristol-Myers Squibb Company (Princeton, N.J.) as GLUCOPHAGE® XR. Additionally, Bristol-Myers Squibb currently distributes a pharmaceutical having a combination of metformin and glyburide as GLUCOVANCE®.

Anti-diabetic agents other than biguanides may also be administered to the identified subject. For example, in alternative embodiments, the anti-diabetic agent may be a thiazolidinedione, such as troglitazone. In some examples, the anti-diabetic agent may be an incretin or dipeptidyl peptidase-4 inhibitor, but in various other examples, the anti-diabetic agent may be any agent of interest.

In embodiments, a therapeutically effective amount of an anti-diabetic agent may be administered in a single dose, or in several doses, for example daily, during a course of treatment. The course of treatment may last for any length of time, such as a day or several days, a week or several weeks, a month or several months, or a year or several years, so long as the therapeutic effect is observed, such as inhibiting the onset of type II diabetes in a subject diagnosed with pre-diabetes, or inducing a subject diagnosed with type 2 diabetes or pre-diabetes to a normal glucose tolerance. In various embodiments, the subject may be monitored while undergoing treatment using the methods described herein in order to assess the efficacy of the treatment protocol. In this manner, the length of time or the amount give to the subject may be modified based on the results obtained using the methods disclosed herein.

In various embodiments, the therapeutically effective amount of the anti-diabetic agent may depend on the anti-diabetic agent being used, the characteristics of the subject being treated (such as age, BMI, physiological condition, etc.), the severity and type of the affliction, and the manner of administration of the agent. The therapeutically effective dose may be determined by various methods, including generating an empirical dose-response curve, predicting potency and efficacy by using quantitative structure activity relationships (QSAR) methods or molecular modeling, and other methods used in the pharmaceutical sciences. In certain, non-limiting examples, the therapeutically effective amount of metformin (or a related biguanide analog or homolog) may be at least about 1000 mg per day, such as at least about 1500 mg per day, or even at least about 1700 mg per day. In certain other, non-limiting examples, the total amount of metformin may be divided into smaller doses, such as two or three doses per day, for example 850 mg twice a day (b.i.d.) or 500 mg three times a day (t.i.d.). In alternative, non-limiting examples, the total amount of metformin may be about 500 mg or less per day. In embodiments, the subject may be monitored at different doses of an agent using the assays described herein in order to determine a therapeutically effective amount for the subject of interest.

For administration to animals or humans, purified therapeutically active agents are generally combined with a pharmaceutically acceptable carrier. Pharmaceutical preparations may contain only one type of anti-diabetic agent, or may be composed of a combination of several types of anti-diabetic agents, such as a combination of two or more anti-diabetic agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers may include, for example, pharmaceutical grades of mannitol, lactose, starch, or magnesium stearate. In addition to biologically-neutral carriers, pharmaceutical compositions to be administered may contain minor amounts of non-toxic auxiliary substances, such as wetting or emulsifying agents, preservatives, and pH buffering agents and the like, for example sodium acetate or sorbitan monolaurate.

Anti-diabetic agents may be administered by any means that achieve their intended purpose. For example, the anti-diabetic agents may be administered to a subject through systemic administration, such as subcutaneous, intravenous or intraperitoneal administration, by suppository, or by oral administration. In embodiments, the anti-diabetic agent may be administered alone or in combination with another anti-diabetic agent. In certain embodiments, the anti-diabetic agent may be administered in the absence of administering any other anti-diabetic agent.

In embodiments, other measures may be taken to inhibit or delay the onset of type II diabetes in subjects at a heightened risk of developing the disease. For example, in some embodiments, a subject may be instructed, trained, or induced to adopt anti-diabetic lifestyle modifications. For example, the subject may be counseled to reduce caloric intake or to exercise. In various embodiments, the methods disclosed herein may be used to monitor the effectiveness of these alternative measures, for instance, to determine if pharmaceutical intervention is warranted for a subject of interest.

VI. Lectins

Lectins are carbohydrate-binding proteins, some of which are specific for particular carbohydrate moieties. The term "lectin" was originally coined to define agglutinins which could discriminate among types of red blood cells, however the term is now used more generally and includes carbohydrate-binding proteins from many sources regardless of their ability to agglutinate cells. Lectins have been found in plants, viruses, microorganisms and animals. Their function in nature is unclear, however lectins share the common property of binding to defined sugar structures.

In embodiments, the glycosylation profile of a sample may be determined by binding to one or more lectins. In some embodiments, the glycosylation profile may be expressed in terms of the lectins to which a sample binds (such as the lectins provided in Table 1, below). The glycosylation profile may also be expressed in terms of the particular carbohydrate modifications present in the sample, based on the carbohydrate-binding specificity of the particular lectins (such as described in Table 1, below) to which the sample binds. However, in embodiments, the identification of specific carbohydrates in a sample may not be essential to determining the glycosylation profile of the sample in the methods described herein.

Similarly, in some embodiments, the glycosylation pattern of a particular protein may be determined by binding to one or more lectins. In some embodiments, the glycosylation pattern of a protein may be expressed in terms of the lectins to which the protein binds (such as the lectins provided in Table 1, below). The glycosylation pattern of the protein may also be expressed in terms of the particular carbohydrate modifications present on the protein, based on the carbohydrate-binding specificity of the particular lectins (such as described in Table 1, below) to which the protein binds, or by other methods known in the art (such as mass spectrometry). However, in embodiments, the identification of specific carbohydrates on the protein may not be essential to determining the glycosylation pattern of the protein in the methods described herein.

Lectins are well known to those of skill in the art. In particular examples, lectins may include *Aleuria aurantia* lectin (AAL), Concanavalin A (Con A), *Datura stramonium* lectin (DSL), *Erythrina cristagalli* lectin (ECL), *Griffonia simplicifolia* lectin II (GSL-2), *Hippeastrum hybrid* lectin (HHL), *Lycopersicon esculentum* lectin (LEL), *Lotus tetragonolobus* lectin (LTL), *Maackia amurensis* lectin I (MAL), *Phaseolus vulgaris* Agglutinin (PHA-E), *Sambucus nigra* lectin (SNA), and *Vicia villosa* lectin (VVL). The binding specificity of exemplary lectins is presented in Table 1, however, the table is not exhaustive and the lectins may also bind to additional carbohydrate modifications.

TABLE 1

Exemplary lectins and binding specificity

| Lectin | Binding specificity |
| --- | --- |
| *Aleuria aurantia* lectin (AAL) | Fucose |
| Concanavalin A (Con A) | Mannose>glucose |
| *Datura stramonium* lectin (DSL) | Gal β1,4 GlcNAc, oligomers of GlcNAc and LacNAc |
| *Erythrina cristagalli* lectin (ECL) | β-gal(1→4)GlcNAc; galactose and galactosides |
| *Griffonia simplicifolia* lectin II (GSL-2) | terminal α-D-galactosyl residues, terminal N-acetyl-α-D-galactosaminyl residues |
| *Hippeastrum* hybrid lectin (HHL) | Mannose |
| *Lycopersicon esculentum* lectin (LEL) | GlcNAc oligomers |
| *Lotus tetragonolobus* lectin (LTL) | Fucose |
| *Maackia amurensis* lectin I (MAL) | N-acetylneuraminic acid (sialic acid) |
| *Phaseolus vulgaris* Agglutinin (PHA-E) | Gal-β1,4 GlcNAc |
| *Sambucus nigra* lectin (SNA) | α-NeuNAc-[2→6]-Gal, α-NeuNAc-[2→6]-GalNAc, α-NeuNAc-[2→3]-Gal |
| *Vicia villosa* lectin (VVL) | O-linked GalNAc |

Additional lectins are well known to one of skill in the art. In some examples, lectins may include *Agaricus bisporus* lectin, *Amaranthus caudatus* lectin, *Griffonia simplicifolia* lectin I, *Bauhinia purpurea* alba lectin, *Codium fragile* lectin, *Dolichos biflorus* lectin, *Erythrina coralldendron* lectin, *Euonymos europaeus* lectin, *Glycine max* lectin, *Helix aspersa* lectin, *Helix pomatia* lectin, *Maclura pomifera* lectin, *Narcissus pseudonarcissus* lectin, *Phaseolus coccineus* lectin, *Phaseolus vulgaris* L lectin, *Phytolacca Americana* lectin, *Pisum sativum* lectin, *Psophocarpus tetragonolobus* I lectin, *Solanum tuberosum* lectin, *Sophora japonica* terminal lectin, *Wisteria floribunda* lectin, *Anguilla anguilla* lectin,

*Arachis hypogaea* lectin, *Artocarpus integrifolia* lectin, *Bandeiraea simplicifolia* lectin, *Caragana arborescens* lectin, *Cicer arietinum* lectin, *Galanthus nicalis* lectin, *Lens culinaris* lectin, *Limulus polyphemus* lectin, *Pseudomonas aeruginosa* lectin, *Ricin communis* agglutinin, *Triticum vulgaris* lectin, *Ulex europaeus* lectin, *Vicia faba* lectin, and *Visum album* lectin. In various embodiments, any lectin that identifies a difference between the glycosylation profile of a sample or the glycosylation pattern of one or more protein from a subject with pre-diabetes, diabetes, or a diabetic complication and a reference may be used in the disclosed methods.

VII. Detection Methods

The methods disclosed herein may be performed in the form of various assay formats, which are well known in the art. In some examples, the assays may be antibody-based or lectin-based assays. There are two main types of assays, homogenous and heterogenous. In homogenous assays, the immunological reaction between an antigen and an antibody (or the reaction between an oligosaccharide and a lectin) and the detection are carried out in a homogenous reaction. Heterogenous assays include at least one separation step, which allows the differentiation of reaction products from unreacted reagents.

ELISA is a heterogenous assay, which has been widely used in laboratory practice since the early 1970s, and may be used in the methods disclosed herein. The assay may be used to detect protein antigens or carbohydrates (such as monosaccharides or oligosaccharides linked to a protein) in various formats. In the "sandwich" format the antigen or carbohydrate being assayed is held between two different antibodies or lectins, respectively. Another type of sandwich assay holds the glycoprotein between an antibody and a lectin.

A sandwich ELISA may be used to detect the presence or amount of an antigen in a sample, such as a glycoprotein (a "protein ELISA"). In this method, a solid surface is first coated with a solid phase antibody. The test sample, containing the antigen (such as a diagnostic glycoprotein), or a composition containing the antigen, such as a urine or saliva sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA may also be used to detect the presence or amount carbohydrates (such as monosaccharides or oligosaccharides, for example in the form of glycoproteins or glycolipids) in a sample by utilizing a lectin in place of an antibody in the assay. In a "lectin ELISA," a solid surface is coated with a lectin. The test sample containing one or more glycosylated biomolecule, such as a urine or saliva sample from a subject of interest, is then added and the carbohydrate in the glycoprotein is allowed to react with the bound lectin. Any unbound glycosylated biomolecule is washed away and a known amount of enzyme-labeled lectin is then allowed to react with the bound antigen. Any excess unbound enzyme-linked lectin is washed away after the reaction. The substrate for the enzyme used in the assay is then added and the reaction between the substrate and the enzyme produces a color change. The amount of visual color change is a direct measurement of specific enzyme-conjugated bound lectin, and consequently the carbohydrate present in the sample tested. A lectin ELISA may not identify the particular biomolecule(s) which is recognized by the lectin, rather a lectin ELISA may provide a glycosylation profile, such as the amount or type of one or more carbohydrate modifications on one or more biomolecule that is present in the sample.

In other examples, an "antibody-lectin ELISA" may be used to detect the presence or amount of carbohydrate modifications on a particular protein in a sample. In this method, a solid surface is first coated with a solid phase antibody. The test sample, containing the antigen (such as A1AG or A1AT), or a composition containing the antigen, such as a urine or saliva sample from a subject of interest, is then added and the antigen is allowed to react with the bound antibody. Any unbound antigen is washed away. A known amount of enzyme-labeled lectin is then allowed to react with the bound antigen. Any excess unbound enzyme-linked lectin is washed away after the reaction. The substrate for the enzyme used in the assay is then added and the reaction between the substrate and the enzyme produces a color change. The amount of visual color change is a direct measurement of specific enzyme-conjugated bound lectin, and consequently the carbohydrate modification present on the particular antigen (the glycosylation pattern of the antigen) in the sample tested.

ELISA may also be used as a competitive assay. In the competitive assay format, the test specimen containing the antigen or oligosaccharide to be determined is mixed with a precise amount of enzyme-labeled antigen or oligosaccharide (such as an enzyme-labeled glycoprotein containing the oligosaccharide) and both compete for binding to an anti-antigen antibody or a lectin attached to a solid surface. Excess free enzyme-labeled antigen or glycoprotein is washed off before the substrate for the enzyme is added. The amount of color intensity resulting from the enzyme-substrate interaction is a measure of the amount of antigen or oligosaccharide in the sample tested.

Similar assays may be performed using alternate platforms for the identification of the glycosylation profile, amount of particular proteins, or glycosylation pattern of particular proteins. For example, microsphere-based assays may be used to detect binding of an antigen to an antibody or a carbohydrate modification to a lectin. Briefly, microsphere beads are coated with an antibody or a lectin and mixed with a sample, such that an antigen or a carbohydrate modification, respectively, present in the sample that are specifically reactive with the antibody or lectin bind to the bead. The bead-bound complexes are allowed to react with fluorescent-dye labeled antibody or lectin, and are measured using a microsphere reader (such as a Luminex instrument). Alternatively, the antibody or lectin may be coupled to a magnetic bead, allowing separation and detection of particular proteins or particular carbohydrate modifications present in the sample.

In additional examples, the glycosylation profile, amount of particular proteins, or glycosylation pattern of particular proteins may be determined with methods utilizing antibody or lectin arrays. For example, the glycosylation profile of a sample may be determined by applying the sample to a lectin array including two or more lectins (for example, two or more of PHA-E, LEL, AAL, ConA, SNA, or MAL) at addressable locations and detecting binding of the sample to particular lectins. The profile of binding of a sample from a subject to the array may be compared to a reference profile (such as a profile from a normal subject) to determine whether the subject is pre-diabetic, diabetic, or has a diabetic complication. Similarly, the amount of particular proteins present in a sample may be determined by applying the sample to an antibody array including two or more antibodies (for example A1AG and A1AT) and detecting binding of the sample to particular antibodies. In additional examples, the glycosylation pattern of particular proteins (for example, A1AG or A1AT) may be determined by applying a sample containing the protein to a lectin array (such as Qproteome GlycoArray, Qiagen, Valencia, Calif.) and detecting binding to particular lectins in the array with a protein-specific antibody.

Other methods for determining the glycosylation profile, amount of glucosylated proteins, or glycosylation pattern of particular proteins may be used. For example, Western blotting may be used to determine the amount of a particular protein in a sample. Similarly, lectin blotting may be used to determine the amount of a particular carbohydrate modification present in a sample, thus providing a glycosylation profile of the sample. The glycosylation pattern of a protein may be determined, for example by immunoprecipitation of a particular protein from a sample, followed by lectin blotting to determine the carbohydrate modifications present on the protein.

VIII. Capture Device Methods

In various embodiments, the disclosed methods may be carried out using a sample capture device, such as a lateral flow device (for example a lateral flow test strip) that allows detection of a glycosylation profile, glycosylation pattern, or amount of protein.

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. The assays are often performed with test strips in which a specific binding pair member is attached to a mobilizable material (such as a metal sol or beads made of latex or glass) or an immobile substrate (such as glass fibers, cellulose strips or nitrocellulose membranes). Particular examples of some of these assays are shown in U.S. Pat. Nos. 4,703,017; 4,743,560; and 5,073,484. The test strips may include a flow path from an upstream sample application area to a test site. For example, the flow path may be from a sample application area through a mobilization zone to a capture zone. The mobilization zone may contain a mobilizable marker that interacts with an analyte or analyte analog, and the capture zone may contain a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances, are found, for example, in U.S. Pat. No. 4,770,853; WO 88/08534; and EP-A 0 299 428. There are a number of commercially available lateral-flow type tests and patents disclosing methods for the detection of large analytes (MW greater than 1,000 Daltons) as the analyte flows through multiple zones on a test strip. Examples are found in U.S. Pat. No. 5,229,073 (measuring plasma lipoprotein levels), and U.S. Pat. Nos. 5,591,645; 4,168,146; 4,366,241; 4,855,240; 4,861,711; 5,120,643; European Patent No. 0296724; WO 97/06439; and WO 98/36278. Multiple zone lateral flow test strips are disclosed in U.S. Pat. Nos. 5,451,504, 5,451,507, and 5,798,273. U.S. Pat. No. 6,656,744 discloses a lateral flow test strip in which a label binds to an antibody through a streptavidin-biotin interaction.

In particular examples, the methods disclosed herein may include application of a biological sample (such as saliva or urine) from a test subject to a lateral flow test device for the detection of a glycosylation profile of the sample. In embodiments, the lateral flow test device may include one or more lectins (such as one or more of PHA-E, LEL, AAL, DSL, ConA, SNA, or MAL) at one or more addressable locations. The addressable locations may be, for example, a linear array or other geometric pattern that provides diagnostic information to the user. The binding of one or more proteins in the sample to the lectins present in the test device may be detected, and the glycosylation profile of the test subject may be compared to the glycosylation profile of a control sample, wherein a change in the glycosylation profile of the sample from the test subject as compared to the control sample indicates that the subject has pre-diabetes, diabetes, or a diabetic complication (such as diabetic nephropathy).

In some examples, the methods disclosed herein may further include determining the amount of one or more proteins (such as one or more protein associated with pre-diabetes or diabetes) in a biological sample (such as saliva or urine) from a test subject by applying the biological sample to a lateral flow test device. The test device may include one or more antibodies (such as anti-A1AG or anti-A1AT) at an addressable location In embodiments, the binding of the proteins in the sample from the test subject to the particular antibodies may be detected, and the amount of the protein in the sample from the test subject may be compared to the amount of the protein in a control sample, wherein a change in the amount of the protein in the sample from the test subject as compared to the control sample may indicate that the subject has pre-diabetes, diabetes, or a diabetic complication (such as diabetic nephropathy).

A. Flow-through Devices

Flow-through type assay devices were designed, in part, to obviate the need for incubation and washing steps associated with dipstick assays. In embodiments, flow-through immunoassay devices may include a capture reagent (such as one or more lectins) bound to a porous membrane or filter to which a liquid sample is added. As the liquid flows through the membrane, target analyte (such as glycoproteins, glycolipids, or proteins) binds to the capture reagent. The addition of sample is followed by (or made concurrent with) addition of detector reagent (such as, labeled (e.g., gold-conjugated, or colored latex particle-conjugated) glycoprotein, labeled (e.g., gold-conjugated or colored latex particle-conjugated) glycolipid or labeled (e.g., gold-conjugate or colored latex particle-conjugated) protein (such as A1AT or A1AG). Alternatively, the detector reagent may be placed on the membrane in a manner that permits the detector to mix with the sample and thereby label the analyte. The visual detection of detector reagent provides an indication of the presence of target analyte in the sample. Representative flow-through assay devices are described in U.S. Pat. Nos. 4,246,339; 4,277,560; 4,632,901; 4,812,293; 4,920,046; and 5,279,935; and U.S. Patent Application Publication Nos. 20030049857 and 20040241876. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534 and European Patent No. EP-A 0 299 428.

There are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte. Additional examples of lateral flow tests for large analytes are disclosed in the following patent documents: U.S. Pat. Nos. 4,168,146; 4,366,241; 4,855,240; 4,861,711; and 5,120,643; European Patent No. 0296724; WO 97/06439; and WO 98/36278. There are also lateral flow type tests for the detection of small analytes (MW 100-1,000 Daltons). Generally, these small analyte tests involve "typical" competitive inhibition to produce negative or indirect reporting results (i.e., reduction of signal with increasing analyte concentration), as exemplified by U.S. Pat. No. 4,703,017. However, several approaches have been developed for detecting small analytes using lateral flow tests that produce positive or direct reporting results (i.e., increase in signal with increasing analyte concentration). These include, for instance, U.S. Pat. Nos. 5,451,504; 5,451,507; 5,798,273; and 6,001,658. U.S. Pat. No. 5,451,504 provides a method with three specific zones (mobilization, trap and detection) each containing a different latex conjugate to yield a positive signal. The mobilization zone contains labeled antibody or lectin to bind the analyte in the sample. In the trap zone, unbound, labeled antibody or lectin is then trapped by immobilized analyte analog. The detection zone captures the labeled analyte-antibody or -lectin complex. U.S. Pat. No. 5,451,507 describes a two-zone, disconnected assay method. The first zone has non-diffusively bound reagent that binds with a component, for example, an analyte analog bound to, or capable of becoming bound to, a member of a signal producing system. The second zone binds to the component only when the analyte to be tested is present. The distance the component migrates into the second zone is directly related to the concentration of analyte. U.S. Pat. No. 5,798,273 discloses a lateral flow device that includes a capture zone with immobilized analyte analog and one or more read-out zones to bind labeled analyte-analog. U.S. Pat. No. 6,001,658 discloses a test strip device with a diffusible, labeled binding partner that binds with analyte, an immobilized analyte, and a detection area containing an immobilized antibody.

Devices described herein generally include a strip of absorbent material (such as a microporous membrane), which, in some instances, may be made of different substances each joined to the other in zones, which may be abutted and/or overlapped. In some examples, the absorbent strip may be fixed on a supporting non-interactive material (such as non-woven polyester), for example, to provide increased rigidity to the strip. Zones within each strip may differentially contain the specific binding partner(s) and/or other reagents required for the detection and/or quantification of the particular analyte being tested for, for example, glycoproteins and/or glycolipids or particular proteins. Thus these zones may be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the glycoproteins and/or glycolipids or particular proteins to be detected may be obtained from any biological source. Examples of biological sources include blood serum, blood plasma, urine, spinal fluid, saliva, fermentation fluid, lymph fluid, tissue culture fluid and ascites fluid of a human or animal. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, may also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

Another common feature to be considered in the use of assay devices is a means to detect the formation of a complex between an analyte (such as a glycoprotein or a glycolipid or one or more particular proteins) and a capture reagent (such as one or more lectins or antibodies). A detector (also referred to as detector reagent) serves this purpose. A detector may be integrated into an assay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte (such as, gold-conjugated lectin for a glycoprotein analyte or a glycolipid analyte or a gold-conjugated antibody for a particular protein). Exemplary lectins are listed in Table 1 above (for example, PHA-E, LEL, AAL, DSL, ConA, SNA, and/or MAL). Exemplary antibodies include, but are not limited to antibodies to A1AG and A1AT. Such antibodies may be commercially available. Exemplary commercially available antibodies include A1AG antibodies (such as catalog numbers sc-59447, sc-51018, sc-51020, Santa Cruz Biotechnology, Santa Cruz, Calif.; catalog number A0011, Dako, Carpinteria, Calif.; catalog numbers ab440, ab17695, Abcam, Cambridge, Mass.) and A1AT antibodies (such as catalog numbers sc-59435, sc-59436, sc-69986, Santa Cruz Biotechnology, Santa Cruz, Calif.; catalog numbers ab7633, ab9400, ab14226, Abcam, Cambridge, Mass.).

In other instances, a detector reagent collectively includes an unlabeled first binding partner specific for the analyte and a labeled second binding partner specific for the first binding partner and so forth. Thus, the detector may be a labeled lectin or antibody specific for a glycoprotein or a glycolipid or a particular protein. The detector may also be an unlabeled first lectin or antibody specific for the glycoprotein or glycolipid or a particular protein and a labeled second antibody that specifically binds the unlabeled first lectin or antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent may specifically recognize a positive control molecule (such as a non-specific human IgG for a labeled Protein A detector, or a labeled Protein G detector, or a labeled anti-human Ab(Fc)) that is present in a secondary capture area.

B. Flow-Through Device Construction and Design

A flow-through device may involve a capture reagent (such as one or more lectins) immobilized on a solid support, typically, microtiter plate or a membrane (such as, nitrocellulose, nylon, or PVDF). Characteristics of useful membrane have been previously described; however, it is useful to note that in a flow-through assay, capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane may be blocked (either before or concurrent with sample administration) to minimize nonspecific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (such as a glycoprotein or glycolipid or one or more particular protein) may specifically bind to the immobilized capture reagent (such as one or more lectins or antibodies). Where detection of an analyte-capture reagent complex is desired, a detector reagent (such as labeled lectin or labeled antibodies that specifically bind glycoproteins, glycolipids, or one or more particular protein) may be added with the sample or a solution containing a detector reagent may be added subsequent to application of the sample. If an analyte is specifically bound by capture reagent, a visual representative attributable to the particular detector reagent may be observed on the surface of the membrane. Optional wash steps may be added at any time in the process, for instance, following application of the sample, and/or following application of a detector reagent.

C. Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte may flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,258,548; 6,699,722; and 6,368,876; EP 0810436; and WO 92/12428; WO 94/01775; WO 95/16207; and WO 97/06439, each of which is incorporated by reference.

Many lateral flow devices are one-step lateral flow assays in which a biological fluid is placed in a sample area on a bibulous strip (though, non-bibulous materials may be used, and rendered bibulous, e.g., by applying a surfactant to the material), and allowed to migrate along the strip until the liquid comes into contact with a specific binding partner (such as a lectin or antibody) that interacts with an analyte (such as one or more glycoprotein, glycolipid, or particular protein) in the liquid. Once the analyte interacts with the binding partner, a signal (such as a fluorescent or otherwise visible dye) indicates that the interaction has occurred. Multiple discrete binding partners (such as lectins or antibodies) may be placed on the strip (for example in parallel lines) to detect multiple analytes (such as glycoproteins, glycolipids, or particular proteins) in the liquid. The test strips may also incorporate control indicators, which provide a signal that the test has adequately been performed, even if a positive signal indicating the presence (or absence) of an analyte is not seen on the strip.

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, NH 03431, (603) 352-3810; both of which are incorporated herein by reference.

Lateral flow devices have a wide variety of physical formats that are equally well known in the art. Any physical format that supports and/or houses the basic components of a lateral flow device in the proper function relationship is contemplated by this disclosure.

Figure 1B:
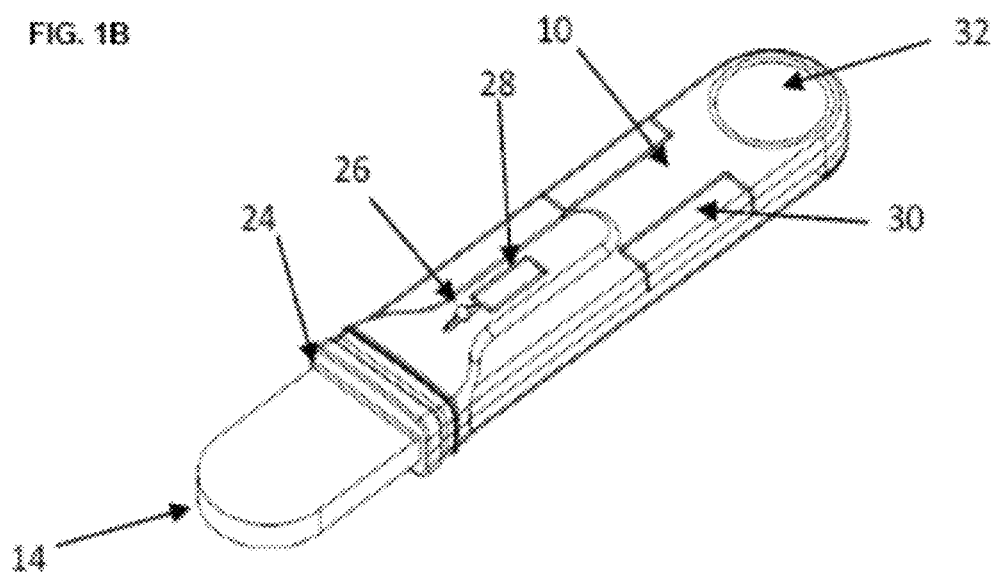
FIG. 1B is a perspective view of an example of a lateral flow device showing the test strip enclosed in a housing, in accordance with various embodiments.

The basic components of a particular embodiment of a lateral flow device are illustrated in FIG. 1A, which shows a particular embodiment of a bibulous lateral flow strip 12. Lateral flow strip 12 is divided into a proximal sample application pad 14, an intermediate test result zone 16, and a distal absorbent pad 18. Flow strip 12 is interrupted by a conjugate pad 19 that contains labeled conjugate (such as gold- or latex-conjugated lectin, antibody, or glycoprotein). A flow path along strip 12 passes from proximal pad 14, through conjugate pad 19, into test result zone 16, for eventual collection in absorbent pad 18. Selective binding agents are positioned on a proximal test line 20 in test result membrane 16. A control line 22 is provided in test result zone 16, slightly distal to test line 20. FIG. 1B illustrates a housing 10 for test strip 12 that includes a rubber syringe dam 24 distal to the proximal sample application pad 14, a sufficiency indicator guide 26, a volumetric indicator 28 distal to the guide, a results window 30, and an grip area 32.

In operation of the particular embodiment of a lateral flow device illustrated in FIG. 1A, a fluid sample containing an analyte of interest, such as one or more glycoprotein, glycolipid, or particular protein of interest, is applied to the sample pad 14. In some examples, the sample may be applied to the sample pad 14 by dipping the end of the device containing the sample pad 14 into the sample (such as urine or saliva) or by applying the sample directly onto the sample pad 14 (for example by placing the sample pad 14 in the mouth of the subject). In other examples where a sample is whole blood, an optional developer fluid is added to the blood sample to cause hemolysis of the red blood cells and, in some cases, to make an appropriate dilution of the whole blood sample.

From the sample pad 14, the sample passes, for instance by capillary action, to the conjugate pad 19. In the conjugate pad 19, the analyte of interest, such as a glycoprotein, glycolipid, or particular protein, may bind (or be bound by) a mobilized or mobilizable detector reagent, such as a glycoprotein (for example fetuin or an affinity-purified lectin binding sample fraction), a lectin (for example one or more of PHA-E, LEL, AAL, DSL, ConA, SNA, or MAL) or an antibody (such as antibody that recognizes A1AG or A1AT). For example, a glycoprotein analyte may bind to a labeled (e.g., gold-conjugated or colored latex particle-conjugated) glycoprotein, lectin or antibody contained in the conjugate pad. The analyte complexed with the detector reagent may subsequently flow to the test result zone 16 where the complex may further interact with an analyte-specific binding partner (such as a lectin, an antibody that binds the lectin, a glycoprotein or other particular protein, an anti-hapten antibody, or streptavidin), which is immobilized at the proximal test line 20. In some examples, a lectin complexed with a detector reagent (such as, gold-conjugated lectin or antibody, labeled (e.g., gold-conjugated) antibody may further bind to unlabeled, oxidized antibodies or lectins immobilized at the proximal test line 20. The formation of a complex, which results from the accumulation of the label (e.g., gold or colored latex) in the localized region of the proximal test line 20 is detected. The control line 22 may contain an immobilized, detector-reagent-specific binding partner, which may bind the detector reagent in the presence or absence of the analyte. Such binding at the control line 22 indicates proper performance of the test, even in the absence of the analyte of interest. The test results may be visualized directly, or may measured using a reader (such as a scanner). The reader device may detect color or fluorescence from the readout area (for example, the test line and/or control line).

In another embodiment of a lateral flow device, there may be a second (or third, fourth, or more) test line located parallel or perpendicular (or in any other spatial relationship) to test line 20 in test result zone 16 (for example test lines 20a, 20b, and 20c in FIG. 1C). The operation of this particular embodiment is similar to that described in the immediately preceding paragraph with the additional considerations that (i) a second detector reagent specific for a second analyte, such as another lectin or antibody, may also be contained in the conjugate pad, and (ii) the second test line will contain a second specific binding partner having affinity for a second analyte, such as a second glycoprotein or glycolipid or a particular protein in the sample. Similarly, if a third (or more) test line is included, the test line will contain a third (or more) specific binding partner having affinity for a third (or more) analyte.

Some of the materials that may be useful for the components of a lateral flow device are shown in Table 2. However, one of skill in the art will recognize that the particular materials used in a particular lateral flow device will depend on a number of variables, including, for example, the analyte to be detected, the sample volume, the desired flow rate and others, and may routinely select the useful materials accordingly.

TABLE 2

Exemplary lateral flow device component materials

| Component | Useful Material |
| --- | --- |
| Sample Pad | Glass fiber |
| | Woven fibers |
| | Screen |
| | Non-woven fibers |
| | Cellulosic filters |
| | Paper |
| Conjugate Pad | Glass fiber |
| | Polyester |

TABLE 2-continued

Exemplary lateral flow device component materials

| Component | Useful Material |
| --- | --- |
| Membrane | Paper |
| | Surface modified polypropylene |
| | Nitrocellulose (including pure nitrocellulose and modified nitrocellulose) |
| | Nitrocellulose direct cast on polyester support |
| | Polyvinylidene fluoride |
| | Nylon |
| Absorbent Pad | Cellulosic filters |
| | Paper |

1. Sample Pad

The sample pad (such as sample pad 14 in FIG. 1A) is a component of a lateral flow device that initially receives the sample, and may serve to remove particulates from the sample. Among the various materials that may be used to construct a sample pad (see Table 2), a cellulose sample pad may be beneficial if a large bed volume (e.g., 250 $\mu l/cm^2$) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

2. Membrane and Application Solution:

The types of membranes useful in a lateral flow device (such as nitrocellulose, nylon and PVDF), and considerations for applying a capture reagent to such membranes have been discussed previously.

3. Conjugate Pad

The conjugate pad (such as conjugate pad 19 in FIG. 1A) serves to, among other things, hold a detector reagent. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad are typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application. In a particular disclosed embodiment, the detector reagent in conjugate pad 19 is gold-conjugated lectin or antibody or a labeled anti-glycoprotein or glycolipid antibody. In another embodiment, the detector reagent includes a lectin binding protein conjugated to a colored latex particle and an additional binding partner (such as biotin or BSA-digoxigenin).

4. Absorbent Pad

The use of an absorbent pad 18 in a lateral flow device is optional. The absorbent pad acts to increase the total volume of sample that enters the device. This increased volume may be useful, for example, to wash away unbound analyte from the membrane. Any of a variety of materials is useful to prepare an absorbent pad, see, for example, Table 2. In some device embodiments, an absorbent pad may be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

IX. Methods for Identifying Compounds That Selectively Block or Alter a Pre-Diabetic or Diabetic Glycosylation Profile The identification herein of altered glycosylation profiles indicative of pre-diabetes, diabetes, and diabetic complications provides an opportunity to identify compounds that prevent such changes in glycosylation profile. Disclosed herein are methods for identifying a compound that selectively decreases or blocks one or more type of glycosylation that is increased in pre-diabetes, diabetes, or diabetic complication, such as one or more type of glycosylation that binds to lectins, such as AAL, DSL, PHA-E, ConA, SNA, LEL, or a combination of two or more thereof.

In some examples, the methods include identifying a compound that selectively binds to one or more type of glycosylation that is increased in pre-diabetes, diabetes, or diabetic complication. In a particular example, a sample with a glycosylation profile indicative of pre-diabetes, diabetes (such as a urine or saliva sample from a subject having pre-diabetes or diabetes) is contacted with a test compound. The sample binding to one or more lectin indicative of pre-diabetes or diabetes (such as AAL, DSL, PHA-E, ConA, SNA, LEL, or a combination of two or more thereof) is determined. A decrease in sample binding to one or more lectin (such as at least a 10% decrease, for example 10%, 20%, 30%, 40%, 50%, 60%, 70%, 80% 90%, or 95% decrease) as compared to a control or reference indicates a compound that selectively binds to one or more type of glycosylation that is increased in pre-diabetes, diabetes, or diabetic complication.

In some examples, a test compound may be administered to a test subject, such as a subject with pre-diabetes or diabetes (such as an animal model, for example, a mouse or rat model of diabetes) for a period of time sufficient to decrease or block one or more type of glycosylation that is increased in pre-diabetes, diabetes, or diabetic complication. One of skill in the art may determine the appropriate time period of treatment for a particular compound. In general, the compound is administered to the subject for at least about one day, two days, five days, one week, two weeks, one month, three months, six months, or more. The glycosylation profile of a sample (such as urine or saliva) from the subject is determined, for example by determining sample binding to one or more lectins. A compound may be considered to decrease or block one or more type of glycosylation associated with pre-diabetes, diabetes, or diabetic complication if it decreases sample binding to one or more lectin (for example, AAL, DSL, PHA-E, ConA, SNA, LEL, or a combination of two or more thereof) by at least about 10% (such as about 10%, 20%, 30%, 40%, 50%, 60%, 70%, 80%, 90%, 95%, or even 99%) as compared to a sample from a subject that is not treated with the test compound.

In embodiments, a "compound" or "test compound" may be any substance or any combination of substances that is useful for achieving an end or result. The compounds identified using the methods disclosed herein may be of use for selectively altering a glycosylation profile associated with pre-diabetes or diabetes. Any compound that has potential (whether or not ultimately realized) to affect glycosylation profile may be tested using the methods of this disclosure.

Appropriate compounds may be contained in libraries, for example, synthetic or natural compounds in a combinatorial library. Numerous libraries are commercially available or may be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or may be readily produced. Additionally, natural or synthetically produced libraries and compounds are readily modified through conventional chemical, physical and biochemical means, and may be used to produce combinatorial libraries. Such libraries are useful for the screening of a large number of different compounds.

Additional test compounds include lectins (for example, AAL, DSL, PHA-E, ConA, SNA LEL, MAL, or ECL), glycosylation inhibitors (for example, N-butyldeoxynojirimycin, castanospermine, 1-deoxymannojirimycin, 1-deoxynorjirimycin, swainsonine, tunicamycin), foods (such as foods containing lectins, for example legumes, such as red kidney beans, soybeans or peanuts), and food extracts (such as fruit or vegetable extracts).

In embodiments, compounds that may alter a glycosylation profile, such as a compound that selectively decreases or blocks one or more type of glycosylation that is increased in pre-diabetes, diabetes, or diabetic complication, may be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration may include powders or granules, suspensions or solutions in water or non-aqueous media, capsules, sachets, or tablets. Thickeners, flavorings, diluents, emulsifiers, dispersing aids or binders may be desirable.

The present disclosure is illustrated by the following non-limiting Examples.

EXAMPLES

Example 1

Glycoproteome Profile in Pre-diabetes and Diabetes

This example describes serum and salivary glycoprotein profiles in control, pre-diabetic, and diabetic subjects.

Methods

Total glycoproteins were enriched from 3 mg of serum or saliva proteins, using Q-proteome glycoprotein fractionation columns (Qiagen, Valencia, Calif.) made of lectins such as ConA, LCH, WGA, and AIL, with standard buffers as provided by the manufacturer. The quantities of the recovered glycoproteins were estimated with a Bio-Rad DC protein assay (Bio-Rad Laboratories, Hercules, Calif.). Samples from five subjects in each representative group were pooled for purification and gel electrophoresis.

Serum or saliva proteins (50 μg) were labeled with CyDye DIGE Fluor minimal dye (Amersham Biosciences, Piscataway, N.J.) at a concentration of 100-400 pmol of dye/50 μg of protein. Samples were labeled with Cy3 (patient), Cy5 (control), or Cy2 (reference, patient+control), and all three labeled samples were multiplexed and resolved in one gel. Labeled proteins were purified by acetone precipitation, dissolved in IEF buffer and rehydrated onto a 24 or 13-cm IPG strip (pH 4-7) for 12 hours at room temperature. The IPG strip was subjected to 1-dimensional electrophoresis at 65-70 kVhrs. The IPG strip was then equilibrated with DTT equilibration buffer and IAA equilibration buffer for 15 minutes sequentially before second-dimensional SDS-PAGE analysis. The IPG strip was then loaded on to an 8-16% SDS-PAGE gel and electrophoresis conducted at 80-90 V for 18 hours to resolve proteins in the second dimension.

Gels were scanned in a Typhoon 9400 scanner (Amersham Biosciences) using appropriate lasers and filters with PMT voltage between 550-600. Images in different channels (control vs. IFG, IGT, and T2 DM) were overlaid using pseudocolors, and differences were visualized using ImageQuant software (Amersham Biosciences). 2D-gel image analysis to determine the differentially abundant protein spots was performed using Phoretix 2D evolution, version 2005 (Non-Linear Dynamics Ltd).

Results

Figure 2A:
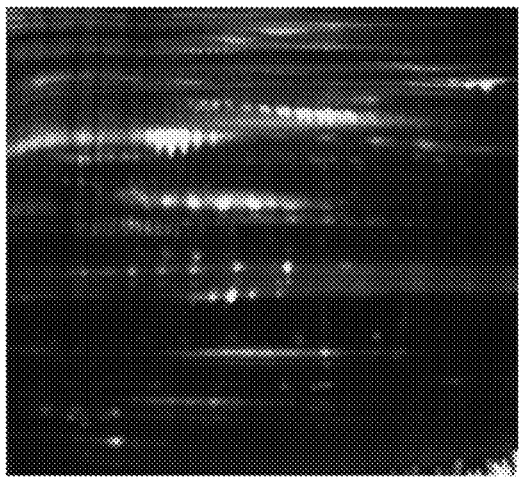
FIG. 2A), impaired fasting glucose (IFG.
Figure 2B:
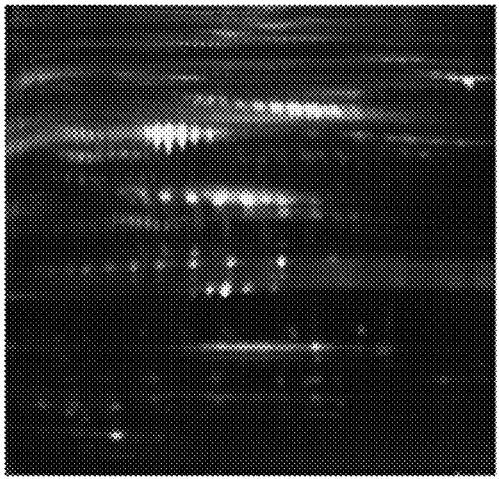
FIG. 2B), type 2 diabetes mellitus (T2DM.
Figure 2C:
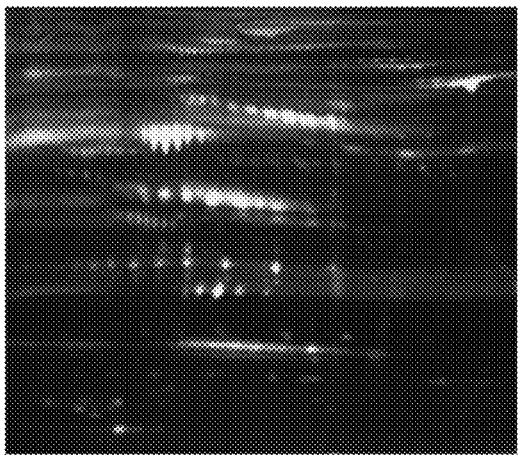
FIG. 2C), or T2DM (FIG. 2D) following treatment labeled with Cy5 (patient) or Cy3 (control) dyes, in accordance with various embodiments.
Figure 2D:
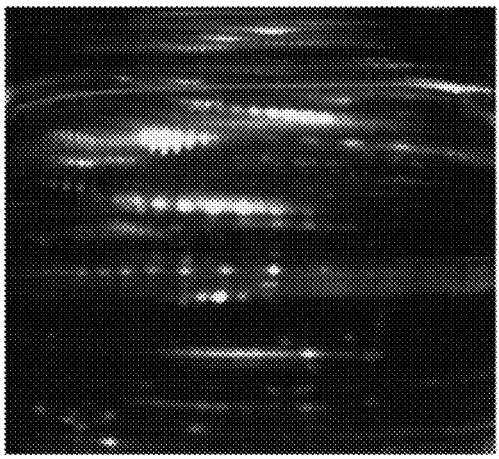
FIG. 2 is a series of digital images showing two-dimensional difference gel electrophoresis of serum glycoproteins from patients with impaired glucose tolerance (IGT.

Two-dimensional difference gel electrophoresis (2D DIGE) analysis was used to analyze serum glycoproteins in samples from patients with IGT (FIG. 2A), IFG (FIG. 2B), and T2DM at diagnosis (FIG. 2C) and T2DM after treatment (FIG. 2D). Equal quantities of labeled proteins were labeled and subjected to 2D DIGE. Distinct changes in the serum glycoproteome profile were observed in the samples. Some glycoprotein spots were increased in IGT, IFG, or T2DM samples compared to controls, while other glycoprotein spots were decreased in IGT, IFG, or T2DM samples compared to controls (FIG. 2).

Salivary glycoproteins were also analyzed by 2D DIGE in samples from patients with IGT (FIG. 3A), IFG (FIG. 3B), T2DM (FIG. 3C), and T1DM (FIG. 3D). As with the serum samples, distinct changes in the salivary glycoproteome profile were observed in the samples. Some glycoprotein spots were increased in IGT, IFG, or T2DM samples compared to controls, while other glycoprotein spots were decreased in IGT, IFG, or T2DM samples compared to controls (FIG. 3). In addition, the analysis showed that some glycoproteins increased in T1DM as compared to T2DM (FIG. 3).

Example 2

Urinary Glycosylation Profile in Pre-diabetes and Diabetes

This example describes the glycosylation profile of urine samples from non-diabetic and pre-diabetic individuals.

Methods

Urine samples were resuspended in 100 mM carbonate-bicarbonate buffer, pH 9.6, coated onto Reactibind™ plates (Pierce, Rockford, Ill.), and incubated overnight at 4° C. On the following day, plates were washed in phosphate buffered saline/Tween (PBST) using a Tecan® microplate washer and incubated with either biotinylated AAL, Con A, DSL, ECL, GSL-2, HHL, LEL, LTL, MAL, PHA-E, SNA, or VVL (Vector Labs, Burlingame, Calif.) diluted in phosphate buffered saline (PBS). Plates were washed with 1.65 ml PBST and incubated with streptavidin-horseradish peroxidase (HRP) (Pierce, Rockford, Ill.) dissolved in PBS. Plates were developed with 3,3',5,5' tetramethylbenzidine (TMB) substrate (Neogen Corporation, Lexington, Ky.) and quenched with 2N $H_2SO_4$. Plates were analyzed using a Spectramax® plus microplate reader (Molecular Devices Corporation, Sunnyvale, Calif.).

Results

A direct lectin ELISA platform was developed to determine changes in specific glycosylation profiles in urine from individuals with pre-diabetes and diabetes. In this platform, urine samples were coated onto an ELISA plate, and global changes in particular types of glycosylation were assessed by probing with biotinylated plant lectins. In the current study, a screen of urine was performed using lectins. Preliminary direct lectin ELISAs were conducted on pooled urine samples from control, pre-diabetes and diabetes individuals. Relatively weak signals were observed for GSL-2 (GlcNAc-GlcNAc), HHL (polymannose), LTL (α-1,2 fucose), and VVL (O-linked GalNac). Strong signals were observed for lectins that recognized lactosamine (Gal-β1,4 GlcNAc), α-1,3 or α-1,6 fucosylation, and terminal sialylation.

Figure 4:
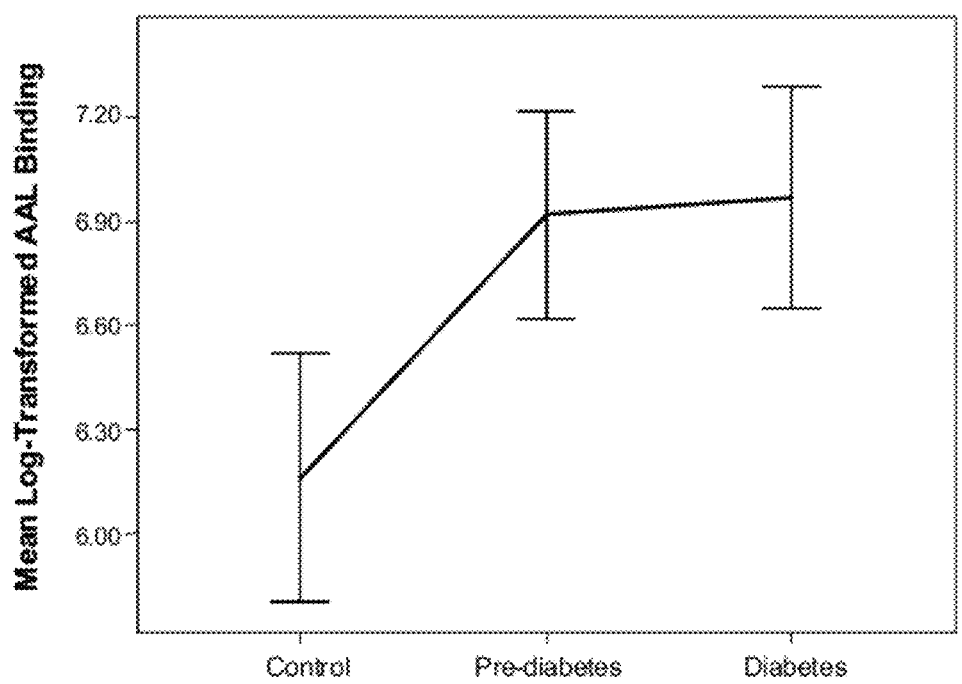
FIG. 4 is a graph of mean log-transformed AAL binding in urine from control, pre-diabetes, and diabetes subjects, in accordance with various embodiments.

A panel of urines from control subjects and patients with pre-diabetes or diabetes was probed. Following normalization by protein concentration, a significantly greater amount of lectin binding was detected in both pre-diabetes and diabetes samples compared to controls using AAL, DSL, and PHA-E biotinylated lectins (Table 3 and FIG. 4). A significantly greater amount of binding by ConA and SNA was also observed in diabetes samples compared to controls (Table 3). The other lectins employed did not detect significant differences between control, pre-diabetic, and diabetic urine samples. However, increased binding by ConA, SNA, and LEL was observed in pre-diabetes samples compared to controls, and increased LEL binding was observed in diabetes samples compared to controls, although these increases were not statistically significant.

TABLE 3

Lectin binding to control, pre-diabetic and diabetic urine samples

| Lectin (arbitrary units) | Study Group (n) | | |
|---|---|---|---|
| | Control (44-50) | Pre-diabetes (49-57) | Diabetes (43-47) |
| AAL | | | |
| Geometric mean (sd) | 473 (3) | 1011 (3) | 1063 (3) |
| p-value[1] | Referent | 0.002 | 0.001 |

TABLE 3-continued

Lectin binding to control, pre-diabetic and diabetic urine samples

| | Study Group (n) | | |
|---|---|---|---|
| Lectin (arbitrary units) | Control (44-50) | Pre-diabetes (49-57) | Diabetes (43-47) |
| DSL | | | |
| Geometric mean (sd)[2] | 472 (3) | 1085 (3) | 1080 (3) |
| p-value[1] | Referent | 0.003 | 0.005 |
| PHA-E | | | |
| Geometric mean (sd) | 12462 (4) | 35118 (7) | 38228 (7) |
| p-value[1] | Referent | 0.02 | 0.02 |
| ConA | | | |
| Geometric mean (sd) | 3507 (59) | 20231 (10) | 53142 (11) |
| p-value[3] | Referent | 0.24 | 0.02 |
| SNA | | | |
| Geometric mean (sd) | 2748 (18) | 6150 (9) | 26680 (3) |
| p-value[3] | Referent | 0.81 | 0.04 |
| LEL | | | |
| Geometric mean (sd) | 2812 (4) | 7328 (7) | 7910 (6) |
| p-value[3] | Referent | 0.13 | 0.07 |
| MAL | | | |
| Geometric mean (sd) | 2171 (3) | 1742 (20) | 3268 (7) |
| p-value[3] | Referent | 0.94 | 0.56 |
| ECL | | | |
| Geometric mean (sd) | 3930 (3) | 5225 (9) | 5738 (9) |
| p-value[3] | Referent | 0.89 | 0.72 |

[1]Linear regression using Generalized Linear Models and Dunnett's 2-sided post-hoc correction factor for multiple comparisons versus the control
[2]Lectin concentration/1000
[3]Linear regression using Generalized Linear Models and Dunnett's T3 post-hoc correction factor to control for unequal variance across study groups Lectin binding by control, pre-diabetic, and diabetic urine samples was also analyzed as a ratio of lectin binding (Table 4). The ratio of SNA binding to MAL binding was significantly increased in diabetes samples compared to controls. The ratio of ConA binding to MAL binding was also significantly increased in diabetes samples compared to controls. The ratio of ConA binding to AAL binding in both pre-diabetes and diabetes samples was increased compared to controls, although this did not reach statistical significance.

TABLE 4

Lectin binding ratio in control, pre-diabetic and diabetic urine samples

| | Study Group (n) | | |
|---|---|---|---|
| Lectin Ratio | Control (43-50) | Pre-diabetes (44-57) | Diabetes (43-47) |
| SNA/MAL | | | |
| Geometric mean (sd) | 1.4 (25) | 3.3 (56) | 18.9 (7) |
| p-value[1] | Referent | 0.77 | 0.001 |
| ConA/MAL | | | |
| Geometric mean (sd) | 1.8 (54) | 11.2 (49) | 29.3 (20) |
| p-value[1] | Referent | 0.17 | 0.003 |
| ConA/AAL | | | |
| Geometric mean (sd) | 17.9 (66) | 89 (11) | 92 (10) |
| p-value[1] | Referent | 0.09 | 0.09 |

[1]Linear regression using Generalized Linear Models and Dunnett's T3 post-hoc correction factor to control for unequal variance across study groups These data provide a glycosylation profile indicative of pre-diabetes. The profile includes significantly increased binding of the sample to the lectins AAL, DSL, PHA-E, or a combination of two or more thereof. In contrast the binding of the sample to ConA, SNA, LEL, MAL, and ECL was not significantly changed compared to the control. Thus, a profile for identifying pre-diabetes may include increased binding of the sample to AAL, DSL, PHA-E or a combination of two or more thereof. The profile may also be expressed as a ranking by amount of lectin binding using the results of a statistical test, such as in increasing order of p-value. Such a glycosylation profile in pre-diabetes may include increased binding to AAL>DSL>PHA-E>LEL>ConA>SNA>ECL>MAL. A glycosylation profile indicative of pre-diabetes may also include increased lectin binding ratios, for example expressed as a ranking of lectin binding ratio in increasing order of p-value. Such a glycosylation profile in pre-diabetes may include increased ConA/AAL>ConA/MAL>SNA/MAL.

These data also provide a glycosylation profile indicative of diabetes. The profile may include increased binding of the sample to the lectins AAL, DSL, PHA-E, ConA, SNA, or a combination of two or more thereof. In contrast, the binding of the sample to LEL, MAL, and ECL was not significantly changed compared to the control. Thus, a profile for identifying diabetes may include increased binding of the sample to AAL, DSL, PHA-E, ConA, SNA, or a combination of two or more thereof. The profile may also be expressed as a ranking by amount of lectin binding using the results of a statistical test, such as in increasing order of p-value. Such a glycosylation profile in diabetes may include increased binding to AAL>DSL>PHA-E=ConA>SNA>LEL>ECL>MAL. A glycosylation profile indicative of diabetes may also include increased lectin binding ratios, such as increased SNA/MAL, ConA/MAL, or a combination thereof. The glycosylation profile of diabetes using lectin binding ratios may also be expressed using the results of a statistical test, such as in increasing order of p-value. Such a glycosylation profile in diabetes may include increased SNA/MAL>ConA/MAL>ConA/AAL ratios.

Example 3

Glycosylation of Alpha-1 Acid Glycoprotein in Pre-diabetes and Diabetes

This example describes the glycosylation pattern (amount and type of glycosylation) of a specific urinary protein in individuals with pre-diabetes and diabetes.

Methods

Concentrations of A1AG in urine were estimated by sandwich ELISA (Clark and Adams, *J. Gen. Virol.* 34:475-483, 1977; Nerurkar et al., *J. Clin. Microbiol.* 20:109-114, 1984). A1AG polyclonal antibody (Dako, Carpinteria, Calif.; cat# A0011) was prepared in 100 mM carbonate-bicarbonate buffer, pH 9.6, at a concentration of 2.0 µg/ml and coated on a Reactibind™ plate by incubating overnight at 4° C. The plate was then washed with PBST and blocked with 3% bovine serum albumin (BSA) in PBS for 1.5 hours at room temperature. After washing the plates with PBST, appropriate dilutions of pure A1AG protein standard (Sigma, St. Louis, Mo.) and urine samples were added to the plate in triplicate and incubated for 1 hour. The plates were incubated with appropriate dilution of biotin-conjugated A1AG Dako polyclonal secondary antibody for 1 hour, and washed with 1.65 ml of PBST. Streptavidin-HRP conjugate was added at a concentration of 0.1 mg/ml and incubated for 45 min prior to washing with PBST. TMB liquid substrate was then added followed by incubation at room temperature for 5-15 min for color development. The reaction was stopped by the addition of 100 µl of 2N $H_2SO_4$. Absorbance at 450 nm was measured on a Spectramax® Plus microplate reader (Molecular Devices Corporation, Sunnyvale, Calif.). A standard curve was generated by either log-log or four-parameter curve fitting using the Softmax® Pro v1.11 software (Molecular Devices Corporation, Sunnyvale, Calif.). The concentrations of the individual samples were estimated from the average values of triplicates, in comparison to the standard curve.

A1AG glycosylation pattern was determined using an antibody-lectin ELISA. A1AG polyclonal antibody was coated onto a Reactibind™ plate as described above. Following blocking with 3% BSA in PBS, the plates were treated with 100 mM sodium metaperiodate, 50 mM citric acid, pH 4 for 15 minutes. Urine samples were added to the plate and incubated for 3 hours at room temperature. Following washing with PBST, biotin-conjugated lectin was added and the plate was incubated at room temperature for 2 hours. Development of the plate was also conducted as described in Example 1.

Results

It was first determined by protein ELISA that A1AG was present in urine in all the pre-diabetic and diabetic conditions. The amount of A1AG in the pre-diabetic IGT and diabetic (NDM) urine was significantly higher than in controls or IFG (Table 5).

The specific types of glycosylation of A1AG were probed with lectins by capturing A1AG on the assay plate and probing the respective sugars with biotinylated lectins (antibody-lectin ELISA; Table 5). A marginal increase in AAL reactivity on A1AG in urine from IGT subjects was observed. There was a significant increase in the ConA reactivity of A1AG in IGT urine compared to control. Lastly, there was a significant difference in the amount of SNA-rective A1AG in NDM urine. Increases in ConA reactivity reflect a greater amount of biantennary content of A1AG, and increases in AAL reactivity indicate a greater amount of terminal fucose.

Example 4

Glycosylation Profile in Diabetic Complications

This example describes the glycosylation profile of urine samples from individuals with diabetic complications, such as chronic renal failure.

Methods

The glycosylation profile of urinary proteins was determined by lectin ELISA, as described in Example 2. Concentrations of A1AG and A1AT in urine were estimated by sandwich ELISA as described in Example 3.

Results

A panel of urines from control subjects and patients with T2DM or T2DM with chronic renal failure (T2DM/renal failure) were probed. The amount of both A1AG and A1AT in both T2DM and T2DM/renal failure urine was significantly higher than in controls (Table 6). A significantly greater amount of lectin binding was detected in both T2DM and T2DM/renal failure samples compared to controls using AAL biotinylated lectin (Table 6). T2DM/renal failure samples also had significantly increased SNA binding compared to controls; however, T2DM samples did not have increased SNA binding compared to controls (Table 6). ConA did not detect significant differences between control, T2DM, and T2DM/renal failure urine samples. The amount of A1AG and A1AT protein, as well as AAL and SNA reactivity was also higher in T2DM/renal failure samples than in T2DM samples.

TABLE 5

A1AG protein and lectin binding to A1AG protein from urine samples

| Analyte | Control (n = 42) Mean ± SD | IFG (n = 16) Mean ± SD | IGT (n = 27) Mean ± SD | NDM (n = 24) Mean ± SD | IGT vs. control p-value | AUROC | NDM vs. control p-value | AUROC |
|---|---|---|---|---|---|---|---|---|
| A1AG | 20.40 ± 6.12 | 32.32 ± 5.17 | 54.71 ± 4.69 | 64.70 ± 2.12 | 0.0379 | 0.669 | 0.0103 | 0.723 |
| A1AG + ConA | 325.47 ± 6.67 | 597.11 ± 9.47 | 855.92 ± 4.77 | 331.94 ± 5.71 | 0.0455 | 0.612 | 0.9663 | 0.528 |
| A1AG + DSL | 678.81 ± 2.84 | 631.41 ± 9.29 | 777.09 ± 8.24 | 510.57 ± 2.92 | 0.7242 | 0.547 | 0.2916 | 0.590 |
| A1AG + AAL | 445.96 ± 2.72 | 604.07 ± 2.21 | 769.75 ± 3.25 | 534.77 ± 2.76 | 0.0566 | 0.613 | 0.4769 | 0.526 |
| A1AG + SNA | 80.13 ± 59.91 | 255.36 ± 50.44 | 440.01 ± 39.64 | 1429.25 ± 13.28 | 0.1000 | 0.626 | 0.0088 | 0.743 |
| A1AG + MAL | 440.60 ± 7.40 | 880.61 ± 3.85 | 977.37 ± 5.09 | 283.06 ± 10.04 | 0.1099 | 0.567 | 0.4144 | 0.589 |

These data provide glycosylation patterns of A1AG in pre-diabetes and diabetes. A glycosylation pattern of A1AG in pre-diabetes may include increased binding of A1AG to the lectins ConA, AAL, or a combination thereof. A glycosylation pattern of A1AG in diabetes may include increased binding of A1AG to the lectin SNA. The A1AG glycosylation pattern may also be expressed as a ranking by amount of lectin binding using the results of a statistical test, such as in increasing order of p-value. Such an A1AG glycosylation pattern in pre-diabetes may include binding to ConA>AAL>MAL>SNA>DSL. An A1AG glycosylation pattern in diabetes may include increased binding to SNA>DSL>MAL>AAL>ConA.

TABLE 6

Lectin binding and protein expression in T2DM and renal failure

|  | Control (n = 10)* | T2DM (n = 20)* | T2DM/Renal Failure (n = 9)* |
|---|---|---|---|
| A1AG |  |  |  |
| Geometric Mean (SD) | 24 (2) | 137 (8) | 7280 (2) |
| P value[1] | Referent | 0.01 | <0.001 |
| A1AT |  |  |  |
| Geometric Mean (SD) | 7 (3) | 109 (11) | 7500 (4) |
| P value[1] | Referent | 0.002 | <0.001 |

TABLE 6-continued

Lectin binding and protein expression in T2DM and renal failure

|  | Control (n = 10)* | T2DM (n = 20)* | T2DM/Renal Failure (n = 9)* |
|---|---|---|---|
| AAL | | | |
| Geometric Mean (SD) | 376 (2) | 774 (2) | 9197 (2) |
| P value[2] | Referent | 0.03 | <0.001 |
| SNA | | | |
| Geometric Mean (SD)[3] | 39 (2) | 70 (3) | 2295 (3) |
| P value[1] | Referent | 0.17 | <0.001 |
| ConA | | | |
| Geometric Mean (SD)[3] | 234 (7) | 93 (4) | 1570 (3) |
| P value[1] | Referent | 0.61 | 0.13 |

*Protein (ng/ml)
[1]Multiple comparisons against the control using Dunnett's T3 post-hoc correction factor to account for unequal variance
[2]2-sided Dunnett's post-hoc correction factor versus the control
[3]Concentration/10,000

These data provide glycosylation profiles for diabetes and the diabetic complication of renal failure. A glycosylation profile in diabetes includes increased binding of the sample to the lectin AAL. A glycosylation profile of a diabetic complication may include increased binding of the sample to the lectins AAL and SNA, or a combination thereof. The glycosylation pattern may also be expressed as a ranking by amount of lectin binding using the results of a statistical test, such as in increasing order of p-value. Such glycosylation profile in diabetes may include binding to AAL>>SNA>ConA. A glycosylation profile in diabetic complication may include increased binding to AAL=SNA>ConA.

Example 5

Exemplary Diagnostic Study

In embodiments, a saliva or urine sample may be obtained from subjects suspected to have pre-diabetes (such as having an OGTT two-hour plasma glucose of greater than or equal to 140 mg/dL and less than 200 mg/dL (7.8-11.0 mM) and/or a fasting plasma glucose (FPG) of greater than 100 mg/dL and less than 126 mg/dL (5.6-6.9 mM)). A lectin ELISA may be performed on the sample, and a glycosylation profile (as defined by binding to one or more particular lectins, such as PHA-E, LEL, DSL, AAL, SNA, ConA, or MAL) may be determined relative to a glycosylation profile in a sample from a control subject without diabetes. A protein ELISA may be performed on the sample, and the amount of A1AG and/or A1AT may be determined relative to the amount of these proteins in a sample from the control.

An analysis may be performed, and the glycosylation profile may be altered compared to the glycosylation profile of the sample from the normal subject. An increase in one or more types of glycosylation in the sample from the subject may identify the subject as pre-diabetic. The glycosylation profile may also be determined relative to the glycosylation profile in a sample from a subject known to be diabetic. An analysis may be performed, and the glycosylation profile may be altered compared to the glycosylation profile of the sample from the diabetic subject. This may confirm that the subject is pre-diabetic.

An analysis may be performed, and the amount of A1AG and/or A1AT may be altered compared to the amount of A1AG and/or A1AT in the sample from the normal subject. An increase in the amount of A1AG and/or A1AT in the sample from the subject may identifie the subject as pre-diabetic. The amount of A1AG and/or A1AT may also be determined relative to the amount of A1AG and/or A1AT in a sample from a subject known to be diabetic. An analysis may be performed, and the amount of A1AG and/or A1AT is altered compared to the amount of A1AG and/or A1AT in the sample from the diabetic subject. This may confirm that the subject is pre-diabetic.

Example 6

Exemplary Lateral Flow Device Diagnostic Test

Figure 5:
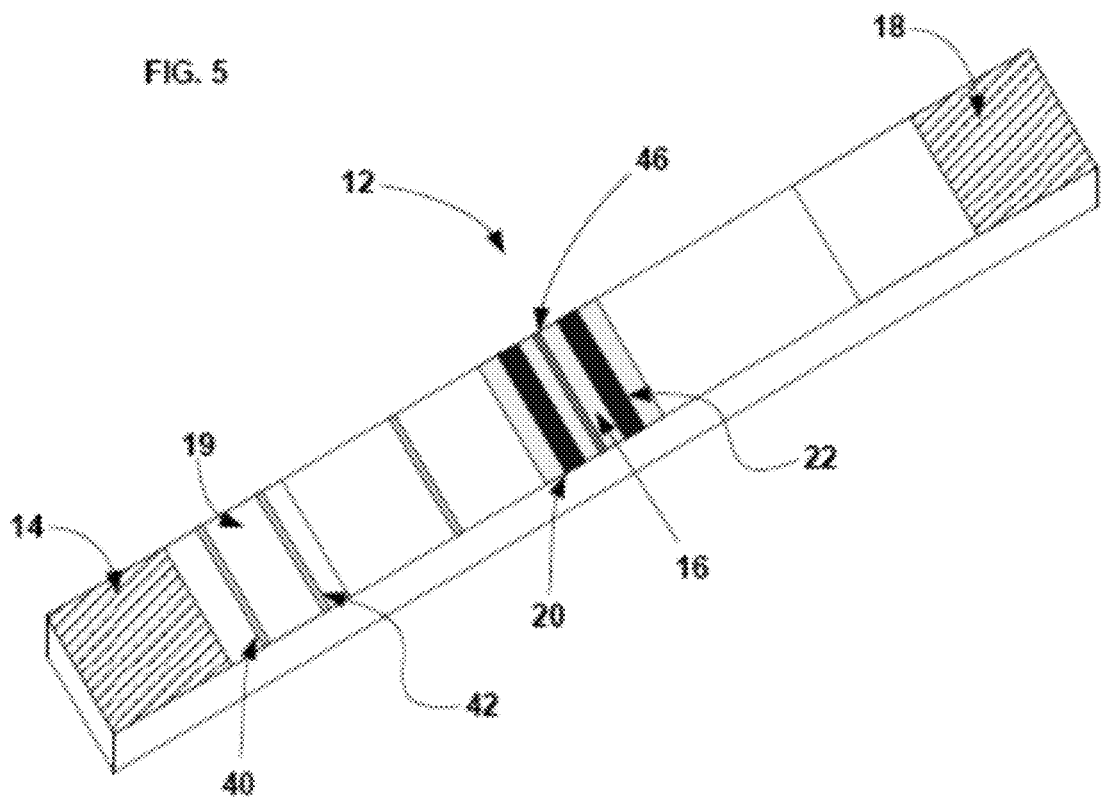
FIG. 5 is a perspective view of an example of a lateral flow test strip for diagnosing pre-diabetes or diabetes, in accordance with various embodiments.

FIG. 5 schematically illustrates an exemplary lateral flow device for diagnosis of pre-diabetes or diabetes, including a test line for pre-diabetes or diabetes and a reference line. The device may detect binding of glycoproteins in a sample to specific glycoprotein-binding molecules using a competitive assay format including a test lectin (TL) and a reference lectin (RL).

In the exemplary device, the conjugate pad 19 may include a test lectin binding protein (TLBP) conjugate 40 (such as the TLBP fetuin covalently attached to blue latex particles and biotin) and a reference lectin binding protein (RLBP) conjugate 42 (such as a protein fraction that is affinity absorbed for TL binding and affinity purified for RL binding covalently attached to blue latex and BSA-digoxigenin). The TL (such as AAL) may be immobilized on the nitrocellulose membrane distal to the conjugate pad at the TL capture line 44. The RL (such as MAL) may be immobilized on the nitrocellulose membrane distal to the TL test line 20 at the RL capture line 46. In embodiments, the TL test line 20 may be streptavidin and the RL test line 22 may be anti-digoxigenin.

The test may be performed by applying a sample (such as urine or saliva) from a subject to the sample application pad 14. The sample may flow through the conjugate pad 19, releasing the TLBP conjugate and the RLBP conjugate. The displaced TLBP conjugate may be captured by the TL test line 20. The displaced RLBP conjugate may be captured by the RL test line 22. The TL test line intensity may be compared to the RL test line intensity (for example, visually or using a reader). If the TL test line intensity is greater than the RL test line intensity, then the subject may be diagnosed as normal. If the TL test line intensity is less than the RL test line intensity, then the subject may be diagnosed as having pre-diabetes or diabetes.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for identifying a subject with a metabolic condition, comprising:
   determining a glycosylation profile of a sample from the subject, wherein the glycosylation profile is determined using a ratio of lectin binding; and
   comparing the glycosylation profile to the glycosylation profile of a sample from a normal control subject, wherein a difference in the glycosylation profile of the sample from the subject as compared to the sample from the normal control subject indicates that the subject has a metabolic condition.

2. The method of claim 1, wherein the metabolic condition is pre-diabetes or diabetes.

3. The method of claim 1, wherein the sample comprises urine, saliva, or serum.

4. The method of claim 1, wherein an increase in a parameter of the glycosylation profile indicates the subject has pre-diabetes or diabetes.

5. The method of claim 1, wherein determining the glycosylation profile of the sample is determined using lectin binding, wherein increased lectin binding indicates that the subject has pre-diabetes or diabetes.

6. The method of claim 5, wherein the lectin is selected from the group consisting of *Aleuria aurantia* lectin, Concanavalin A, *Datura stramonium* lectin, *Erythrina cristagalli* lectin, *Lycopersicon esculentum* lectin, *Maackia amurensis* lectin I, *Phaseolus vulgaris* agglutinin, and *Sambucus nigra* lectin.

7. The method of claim 5, wherein increased lectin binding by *Aleuria aurantia* lectin, *Datura stramonium* lectin, or *Phaseolus vulgaris* agglutinin indicates the subject has pre-diabetes.

8. The method of claim 5, wherein increased lectin binding by Concanavalin A or *Sambucus nigra* lectin indicates the subject has diabetes.

9. The method of claim 1, wherein the ratio of lectin binding is a ratio of *Sambucus nigra* lectin to *Maackia amurensis* lectin I, a ratio of Concanavalin A to *Maackia amurensis* lectin I, or a ratio Concanavalin A to *Aleuria aurantia* lectin.

10. The method of claim 9, wherein an increase in the ratio of *Sambucus nigra* lectin to *Maackia amurensis* lectin I or an increase in the ratio of Concanavalin A to *Maackia amurensis* lectin I indicates the subject has diabetes.

11. The method of claim 1, further comprising determining a quantity of alpha-1 acid glycoprotein (A1AG) and/or alpha-1 antitrypsin (A1AT) protein in the sample from the subject, wherein a difference in the quantity of the alpha-1 acid glycoprotein (A1AG) and/or alpha-1 antitrypsin (A1AT) protein in the sample from the subject as compared to the sample from the normal control subject indicates that the subject has pre-diabetes or diabetes.

12. The method of claim 11, wherein an increase in the quantity of A1AG, A1AT, a ratio of A1AG to A1AT, or a combination thereof, as compared to the control sample indicates that the subject has pre-diabetes or diabetes.

13. The method of claim 11, wherein determining the quantity of the alpha-1 acid glycoprotein (A1AG) and/or alpha-1 antitrypsin (A1AT) protein comprises an immunoassay.

14. The method of claim 1, further comprising:
   determining a glycosylation pattern of alpha-1 acid glycoprotein (A1AG) and/or alpha-1 antitrypsin (A1AT) in the sample from the subject; and
   comparing the glycosylation pattern of the alpha-1 acid glycoprotein (A1AG) and/or alpha-1 antitrypsin (A1AT) in the sample to the glycosylation pattern of the alpha-1 acid glycoprotein (A1AG) and/or alpha-1 antitrypsin (A1AT) in a sample from a normal control subject, wherein a difference in the glycosylation profile or glycosylation pattern in the sample from the subject as compared to the sample from the normal control subject indicates that the subject has pre-diabetes or diabetes.

15. The method of claim 14, wherein determining the glycosylation pattern of the alpha-1 acid glycoprotein (A1AG) and/or alpha-1 antitrypsin (A1AT) is determined using lectin binding, wherein increased lectin binding indicates that the subject has pre-diabetes or diabetes.

16. The method of claim 15, wherein the lectin comprises one or more lectins that bind alpha-1 acid glycoprotein.

17. The method of claim 16, wherein the lectin comprises one of more of Concanavalin A, *Aleuria aurantia* lectin, or *Sambucus nigra* lectin.

18. The method of claim 17, wherein increased lectin binding by Concanavalin A or *Sambucus nigra* lectin indicates the subject has pre-diabetes.

19. The method of claim 14, further comprising determining a quantity of alpha-1 acid glycoprotein (A1AG) and/or alpha-1 antitrypsin (A1AT) protein in the sample from the subject.

20. The method of claim 19, wherein an increase in the quantity of A1AG, A1AT, a ratio of A1AG to A1AT, or a combination thereof, as compared to the control sample indicates that the subject has pre-diabetes or diabetes.

21. The method of claim 19, wherein determining the quantity of the alpha-1 acid glycoprotein A1AG and/or alpha-1 antitrypsin (A1AT) protein comprises an immunoassay.

22. The method of claim 1, wherein determining a glycosylation profile of a sample from the subject comprises contacting a sample from the subject with a lateral flow device comprising one or more lectins.

23. The method of claim 22, wherein the one or more lectins is selected from the group consisting of *Aleuria aurantia* lectin, Concanavalin A, *Datura stramonium* lectin, *Erythrina cristagalli* lectin, *Lycopersicon esculentum* lectin, *Maackia amurensis* lectin I, *Phaseolus vulgaris* agglutinin, and *Sambucus nigra* lectin.

24. The method of claim 1, wherein the metabolic condition is a diabetic complication.

25. The method of claim 24, wherein the diabetic complication is a microvascular complication or a macrovascular complication.

26. The method of claim 25, wherein the microvascular complication comprises one or more of diabetic nephropathy, diabetic retinopathy, or diabetic neuropathy.

27. The method of claim 24, wherein the glycosylation profile is determined using lectin binding, wherein increased lectin binding indicates that the subject has the diabetic complication.

28. The method of claim 27, wherein increased lectin binding by *Aleuria aurantia* lectin or *Sambucus nigra* lectin indicates the subject has the diabetic complication.

29. The method of claim 24, further comprising determining a quantity of alpha-1 acid glycoprotein (A1AG) and/or alpha-1 antitrypsin (A1AT) protein in the sample from the subject, wherein a difference in the quantity of the alpha-1 acid glycoprotein (A1AG) and/or alpha-1 antitrypsin (A1AT) protein in the sample from the subject as compared to the sample from the normal control subject indicates that the subject has a diabetic complication.

* * * * *